US009795686B2

(12) United States Patent
Lee et al.

(10) Patent No.: US 9,795,686 B2
(45) Date of Patent: Oct. 24, 2017

(54) BIOMATERIALS COMPRISING HYALURONIC ACID BINDING PEPTIDES AND BIFUNCTIONAL BIOPOLYMER MOLECULES FOR HYALURONIC ACID RETENTION AND TISSUE ENGINEERING APPLICATIONS

(71) Applicant: THE JOHNS HOPKINS UNIVERSITY, Baltimore, MD (US)

(72) Inventors: Janice Lee, Baltimore, MD (US); Jennifer H. Elisseeff, Baltimore, MD (US); Shimon A. Unterman, Brookline, MA (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 247 days.

(21) Appl. No.: 14/372,258

(22) PCT Filed: Jan. 22, 2013

(86) PCT No.: PCT/US2013/022502
§ 371 (c)(1),
(2) Date: Jul. 15, 2014

(87) PCT Pub. No.: WO2013/110056
PCT Pub. Date: Jul. 25, 2013

(65) Prior Publication Data
US 2014/0369975 A1    Dec. 18, 2014

Related U.S. Application Data

(60) Provisional application No. 61/588,302, filed on Jan. 19, 2012.

(51) Int. Cl.
| | | |
|---|---|---|
| *A61K 47/00* | (2006.01) | |
| *A61K 47/48* | (2006.01) | |
| *A61K 9/06* | (2006.01) | |
| *A61K 47/36* | (2006.01) | |
| *A61K 47/42* | (2017.01) | |
| *A61L 27/26* | (2006.01) | |
| *A61L 27/38* | (2006.01) | |
| *A61L 27/52* | (2006.01) | |
| *A61K 35/12* | (2015.01) | |
| *A61K 9/00* | (2006.01) | |
| *A61K 47/10* | (2017.01) | |

(52) U.S. Cl.
CPC ...... *A61K 47/48338* (2013.01); *A61K 9/0019* (2013.01); *A61K 9/0024* (2013.01); *A61K 9/06* (2013.01); *A61K 35/12* (2013.01); *A61K 47/10* (2013.01); *A61K 47/36* (2013.01); *A61K 47/42* (2013.01); *A61K 47/48215* (2013.01); *A61L 27/26* (2013.01); *A61L 27/3817* (2013.01); *A61L 27/3834* (2013.01); *A61L 27/52* (2013.01); *A61L 2430/06* (2013.01); *A61L 2430/10* (2013.01); *A61L 2430/16* (2013.01)

(58) Field of Classification Search
None
See application file for complete search history.

(56) References Cited

U.S. PATENT DOCUMENTS

2014/0369975 A1* 12/2014 Lee .................. A61K 9/06
424/93.7
2016/0158270 A1*  6/2016 Singh ............... A61K 9/0019
514/16.8

FOREIGN PATENT DOCUMENTS

JP       2006-500953 A    1/2006

OTHER PUBLICATIONS

Unterman, S et al "Hyaluronic Acid-Binding Scaffold for Articular Cartilage Repair" Tissue Eng Part A. Dec. 2012 (e-pub. Aug. 14, 2012); 18(23-24): 2497-2506. DOI: 10.1089/ten.tea.2011.0711.*
Ali, M., et al., "Controlled release of high molecular weight hyaluronic acid from molecularly imprinted hydrogel contact lenses", Pharmaceutical Research (2009) vol. 26, No. 3, pp. 714-726.

(Continued)

*Primary Examiner* — Chris R Tate
*Assistant Examiner* — Aaron J Kosar
(74) *Attorney, Agent, or Firm* — Johns Hopkins Technology Transfer

(57) ABSTRACT

The present invention provides novel biomaterial compositions and methods having a technology to improve retention of hyaluronic acid (HA). The biomaterial compositions utilize small HA binding peptides that is tethered to synthetic biocompatible polymers. When tethered to the polymers, the peptide region allows the polymers to bind to HA. The biocompatible polymers are modified to contain a crosslinking group so that the HA can be incorporated into a scaffold and retained in place. The novel biomaterial 1 compositions can be made into hydrogel compositions and used in a variety of tissue applications, using mild crosslinking conditions and they also have the ability to be degraded with hyaluronidase if needed. Furthermore, the novel biomaterial compositions will enable enhanced interaction between the scaffold and encapsulated cells for a wide variety of tissue engineering applications. Methods of making hydrogel compositions and their use are also provided. The present invention also provides bifunctional biopolymer compositions comprising a biologically compatible polymer having at least one amine reactive moiety and at least one thiol reactive moiety and provides thiolated HA binding peptides which can be used together to coat or chemically modify cartilage or tissues having amine reactive residues with a biologically compatible polymer having HA binding peptides, which allow HA to bind to the surface of the cartilage or tissues. Methods of using same are also provided.

15 Claims, 13 Drawing Sheets

(56) References Cited

OTHER PUBLICATIONS

Mummert, M., et al., "Development of a peptide inhibitor of hyaluronan-mediated leukocyte trafficking", The Journal of Experimental Medicine, (2000) vol. 192, No. 6, pp. 769-779.
Heredia, K., et al., "Synthesis of protein-polymer conjugates", Organic & Biomolecular Chemistry, (2007) vol. 5 pp. 45-53.
Park, Y., et al., "Photopolymerized hyaluronic acid-based hydrogels and interpenetrating networks", Biomaterials, (2003) vol. 24, pp. 893-900.

* cited by examiner

```
                         SEQUENCE LISTING

<160> NUMBER OF SEQ ID NOS: 15

<210> SEQ ID NO 1
<211> LENGTH: 12
<212> TYPE: PRT
<213> ORGANISM: Artificial Sequence
<220> FEATURE:
<223> OTHER INFORMATION: Synthetic Sequence

<400> SEQUENCE: 1

Gly Ala His Trp Gln Phe Asn Ala Leu Thr Val Arg
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic sequence

<400> SEQUENCE: 2

Cys Arg Arg Asp Asp Gly Ala His Trp Gln Phe Asn Ala Leu Thr Val
1               5                   10                  15

Arg

<210> SEQ ID NO 3
<211> LENGTH: 12
<212> TYPE: PRT
<213> ORGANISM: Artificial Sequence
<220> FEATURE:
<223> OTHER INFORMATION: Synthetic sequence

<400> SEQUENCE: 3

Gly Ala Ala Trp Gln Phe Asn Ala Leu Thr Val Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic sequence

<400> SEQUENCE: 4

Gly Ala His Trp Gln Phe Ala Ala Leu Thr Val Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic sequence

<400> SEQUENCE: 5

Gly Ala His Trp Gln Phe Asn Ala Leu Thr Val Ala
1               5                   10

<210> SEQ ID NO 6
```

-continued

```
<211> LENGTH: 18
<212> TYPE: DNA
<213> ORGANISM: Artificial Sequence
<220> FEATURE:
<223> OTHER INFORMATION: Synthetic sequence

<400> SEQUENCE: 6
ggcacccagc acaatgaa                                                      18

<210> SEQ ID NO 7
<211> LENGTH: 21
<212> TYPE: DNA
<213> ORGANISM: Artificial Sequence
<220> FEATURE:
<223> OTHER INFORMATION: Synthetic sequence

<400> SEQUENCE: 7
gctaacagtc cgcctagaag c                                                  21

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8
cacgatgcct ttcaccacga c                                                  21

<210> SEQ ID NO 9
<211> LENGTH: 21
<212> TYPE: DNA
<213> ORGANISM: Artificial Sequence
<220> FEATURE:
<223> OTHER INFORMATION: Synthetic sequence

<400> SEQUENCE: 9
tgcgggtcaa cagtgcctat c                                                  21

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
agggccaaga cgaagacatc                                                    20

<210> SEQ ID NO 11
<211> LENGTH: 21
<212> TYPE: DNA
<213> ORGANISM: Artificial Sequence
<220> FEATURE:
<223> OTHER INFORMATION: Synthetic sequence

<400> SEQUENCE: 11
agatcacgtc atcgcacaac a                                                  21

<210> SEQ ID NO 12
<211> LENGTH: 21
<212> TYPE: DNA
<213> ORGANISM: Artificial Sequence
<220> FEATURE:
<223> OTHER INFORMATION: Synthetic sequence

<400> SEQUENCE: 12
```

```
gtggagcagc aagagcaagg a                                                21

<210> SEQ ID NO 13
<211> LENGTH: 21
<212> TYPE: DNA
<213> ORGANISM: Artificial Sequence
<220> FEATURE:
<223> OTHER INFORMATION: Synthetic sequence

<400> SEQUENCE: 13
cttgccccac ttaccagtgt g                                                21

<210> SEQ ID NO 14
<211> LENGTH: 20
<212> TYPE: DNA
<213> ORGANISM: Artificial Sequence
<220> FEATURE:
<223> OTHER INFORMATION: Synthetic sequence

<400> SEQUENCE: 14
cgaggaggcc ccggaacaga                                                  20

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
gcacctcgct catgccggag                                                  20
```

BIOMATERIALS COMPRISING HYALURONIC ACID BINDING PEPTIDES AND BIFUNCTIONAL BIOPOLYMER MOLECULES FOR HYALURONIC ACID RETENTION AND TISSUE ENGINEERING APPLICATIONS

REFERENCE TO RELATED APPLICATIONS

This application claims the benefit of PCT Application No. PCT/US2013/022502, filed Jan. 22, 2013, which claims the benefit of U.S. Provisional Patent Application No. 61/588,302, filed on Jan. 19, 2012, both of which are hereby incorporated by reference for all purposes as if fully set forth herein.

STATEMENT OF GOVERNMENTAL INTEREST

This invention was made with government support under grant no. EB005517 and AG328232 awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Jul. 14, 2014, is named P10108-05_ST25.txt and is 3,462 bytes in size.

BACKGROUND OF THE INVENTION

Hyaluronic acid (HA) is used extensively in tissue engineering scaffolds due to its important structural and signaling roles in a variety of tissues, including the joint. It is a nonsulfated glysocaminoglycan (GAG) composed of repeating disaccharide units of glucuronic acid and N-acetylglucosamine. The carboxylate group of glucuronic acid allows for relatively facile crosslinking and chemical modification of HA forming hydrogels or sponges, which has led to its evaluation as a scaffold material for a variety of tissues. However, the resultant HA-based scaffolds exhibit little similarity with the natural structure and presentation of HA found in the body. The bioactivity of HA is highly dependent on the molecular weight of the polymer and its associations with other proteins and extracellular matrix (ECM) components, and it is unclear how crosslinked HA scaffolds would affect cellular behavior compared to its natural presentation. Furthermore, the covalent modification of the HA backbone itself may significantly change its biological activity in unanticipated ways. A more natural, biologically relevant presentation of the HA may yield greater insight into the effects of HA-based scaffolds for tissue engineering, and may better potentiate tissue repair.

Cartilage tissue engineering aims to develop an effective therapy to repair articular cartilage lost due to trauma or disease. Cartilage has poor endogenous repair capacity, and currently available therapies are largely ineffective at producing a robust, healthy repair tissue. Given the aging population and increasing incidence of cartilage damage and osteoarthritis, there is significant interest in cartilage repair and restoring joint function. Biomaterials play an important role in serving as a scaffold to direct tissue repair. Tissue engineering scaffolds normally are composed of combinations of biological and synthetic polymer systems. While biological polymer systems often exhibit good bioactivity and regeneration potential, they frequently are mechanically weak, and difficult to control and purify. Attempts to chemically modify biological polymers to increase scaffold strength and control are often challenging and may cause a loss of biological activity. In contrast, synthetic systems boast a high degree of control over physical properties but exhibit little to no biological activity. Of recent interest is the combination of synthetic materials with biologically active molecules in order to form bio-synthetic composite materials that share the high degree of control found in synthetic materials with the biological functionalities found in biological polymers. These composite biomaterials include synthetic polymers modified with bioactive proteins or peptides to introduce specific biological functionalities such as cell adhesion, growth factor activity, or cell-mediated degradation.

Lubrication in tissues is also important to maintain a low-friction movement within a number of biological systems, including the pleural cavity, the surface of the eye, and diarthroidal joints. In diarthrodial joints, healthy painless movement is facilitated by both molecules at the tissue surface and in the lubricating synovial fluid. Synovial fluid bathes the joint surface with several molecules that contribute to boundary lubrication including lubricin, surface active phospholipids, and HA. The role of each of these components has been supported and challenged on the basis of various in vitro studies on cartilage lubrication, however in a healthy joint these molecules work together synergistically to reduce friction coefficients in boundary lubrication to achieve normal physiological performance. Today, therapeutic options to enhance tissue lubrication focus only on replacing or enhancing the lubricant in the fluid phase.

The breakdown of joint lubrication is a major hallmark of osteoarthritis (OA), stimulating significant interest in understanding and enhancing joint lubrication to improve overall joint health. Only ~10% of the cartilage surface area comes into direct contact with the opposite surface during walking in the healthy knee, suggesting the role of boundary lubrication is relatively small. Osteoarthritic knees are further challenged by narrow intra-articular spaces, roughened cartilage surfaces, and often abnormal joint motion. All of these contribute to a much greater reliance on boundary lubrication at the same time that many boundary lubricants are depleted and disrupted by inflammatory processes. The resultant higher friction leads to pain, accelerated degeneration of cartilage, and disease progression. HA is believed to improve joint lubrication through its viscoelastic properties at high molecular weights, although biological functions may also play a role. As a result, one common clinical treatment for OA is injection of HA directly into the joint to improve synovial lubrication. Despite the physical and biological attributes of HA, clinical results of HA injections have been inconclusive and suspect due to the clearly observable rapid turnover of HA molecules within the joint after injection and limited ability to target areas where increased lubrication is needed.

The major limitation of HA implantation and use in lubrication in a joint or in cartilaginous tissues, however, is its longevity. For example, it has been shown that when injected into a joint, HA remains only for 24 hours.

Hence, the duration of an enhancement/repair/treatment achieved with hydrogel compositions is limited in time, and frequently requires the recipient to undergo additional and expensive repeat injections/treatments to maintain a desired effect. Hence, a need continues to exist in the tissue repair and reconstructive arts for improved HA containing biomaterial compositions which improve retention of HA in the hydrogel and are longer lasting.

SUMMARY OF THE INVENTION

HA-binding peptides have been shown to interact specifically with native HA under physiological condition. Previously, HA-binding peptides have been used only to inhibit the glycosaminoglycan-mediated signaling. The novelty of the present inventions includes the use the HA-binding peptide to retain HA in space and ensure interaction between synthetic scaffolds and encapsulated biological molecules.

In accordance with an embodiment, the present invention provides a biomaterial comprising at least one biologically compatible polymer having one or more HA binding peptides covalently linked to the biologically compatible polymer, and at least one other component.

In an embodiment of the present invention, HABPep was conjugated to a synthetic hydrogel scaffold based on poly (ethylene glycol) diacrylate (PEGDA) and the resulting biomaterial's ability to interact with HA was investigated using an in vitro model system. This scaffold can interact with HA in the local ECM environment, including cell-secreted HA and exogenously supplied HA. It was found that this HA-interacting hydrogel improves chondrogenesis of bone marrow-derived mesenchymal stem cells (MSCs) in an in vitro culture system since HA is a key molecule in cartilage matrix.

In addition, in one or more alternative embodiments, the inventors found that localizing HA to the surface of articular cartilage enhances the boundary lubrication effects of free HA in the synovial fluid, and mimics the presumed role of lubricin to improve joint lubrication in a healthy knee. In addition, HA has a number of biological functions that would be ideal to concentrate at the tissue surface including reducing inflammation, mediating matrix metalloproteinase expression and protecting cells from radical damage. Thus, in one or more embodiments, the novel biomaterial includes a coating for a tissue surface with HA that can also physically protect the cartilage surface from cytokines and degrading enzymes that are frequently found in a diseased or post-truamatic joint. Finally, and most critically, the presence of the polymer-HA binding modification provides a self-healing mechanism to concentrate HA on a tissue surface.

In accordance with one or more embodiments, the present invention provides new and improved biomaterial compositions in which the biomaterial is in the form of a cross-linked hydrogel which comprises a HA binding peptide (HABPep) that significantly improves the retention of HA in the hydrogel and which resists degradation with hyaluronase treatment. This HABPep improves the retention of HA in the implantation site, and can be easily further modified for other applications.

In accordance with an embodiment, the present invention provides a hydrogel composition comprising: a) one or more first biocompatible polymers having one or more HA binding peptides (HABPep) which are covalently linked to the first biocompatible polymers; and b) one or more second biocompatible polymers; wherein the biocompatible polymers of a) and b) are cross linked together to form a hydrogel.

In accordance with another embodiment, the present invention provides a method of filling a void on or in a subject, said method comprising contacting said void with the biomaterial compositions described herein.

In accordance with an embodiment, the present invention provides a method of treating a cartilage defect in a tissue of a subject comprising administering to the tissue of the subject in need of treatment, a therapeutically effective amount of the biomaterial compositions described herein.

In accordance with a further embodiment, the present invention provides a therapeutic method for the treatment of eye diseases by means of an eye surgery treatment, comprising applying to the eye of a subject in need of such treatment a therapeutically effective amount of the biomaterial compositions described herein.

In accordance with still another embodiment, the present invention provides a therapeutic method for the treatment of dry eye in a subject comprising applying to the eye of a subject in need of such treatment a therapeutically effective amount of the biomaterial compositions described herein.

In accordance with an embodiment, the present invention provides a method for making the hydrogel compositions described herein, comprising: a) obtaining a sufficient amount of one or more first biocompatible polymers in a N-succinamideN-succinimide form in a suitable bicarbonate solution; b) obtaining a sufficient amount of having one or more HA binding peptides (HABPep) in a suitable bicarbonate solution; c) adding the solution of b) to the solution of a) and mixing for a sufficient period of time to produce one or more first biocompatible polymers having one or more HA binding peptides (HABPep) which are covalently linked to the first biocompatible polymers; d) removing unreacted first biocompatible polymers and HABPep; e) purifying the product of c); f) adding a sufficient amount of the product of c) to a solution comprising a sufficient amount second biocompatible polymer in a suitable solvent; g) adding to f) a sufficient amount of a photoinitiating agent; h) exposing the solution of g) to electromagnetic radiation at a sufficient wavelength and intensity to initiate photopolymerization of the solution to produce the hydrogel composition; i) removing the unreacted reagents off) and g) and purify the remaining product of h).

In accordance with an embodiment, the present invention provides a bifunctional biopolymer composition comprising a biologically compatible polymer having at least one amine reactive moiety and at least one thiol reactive moiety.

In accordance with an embodiment, the present invention provides a method for coating a tissue surface with a biologically compatible polymer having one or more HA binding peptides comprising: a) contacting the tissue surface with an effective amount of the bifunctional biopolymer composition described herein for a time sufficient to create a thiol reactive tissue surface; and b) contacting the tissue surface of a) with an effective amount of thiolated HA binding peptides to create a tissue surface coated with a biologically compatible polymer having one or more HA binding peptides.

In accordance with an embodiment, the present invention provides a method of treating a cartilage defect in a tissue of a subject comprising: a) administering to the tissue of the subject in need of treatment, an effective amount of the bifunctional biopolymer composition described herein for a time sufficient to create a thiol reactive tissue surface on the cartilage defect; and b) administering to the tissue of the subject in need of treatment, an effective amount of thiolated HA binding peptides to create a cartilage defect coated with a biologically compatible polymer having one or more HA binding peptides.

Figure 1:
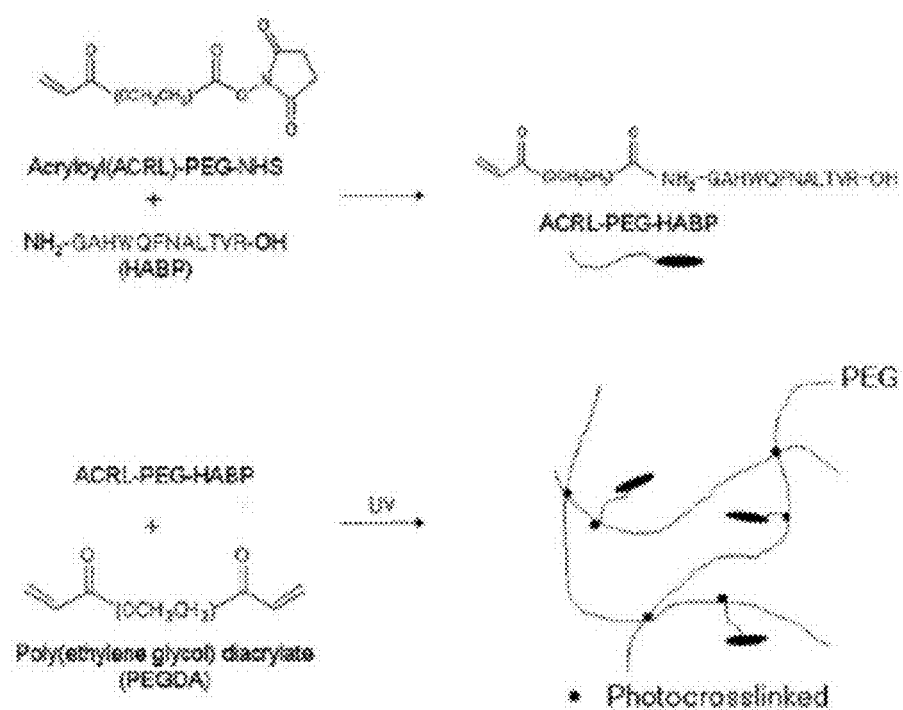
FIG. 1 is a schematic depiction of an embodiment of a method for producing the hydrogel biomaterial compositions of the present invention. HA-binding peptide (GAH-WQFNALTVR) (SEQ ID NO: 1) was synthesized by Fmoc chemistry and purified by High performance liquid chromatography (HPLC). Synthesis and purification have been confirmed by MALDI-TOF. HA-binding peptide has been crosslinked to poly(ethylene glycol) acrylate and photopolymerized along with Poly (ethylene glycol) diacrylate (PEGDA). The product is a clear hydrogel.
Figure 2:
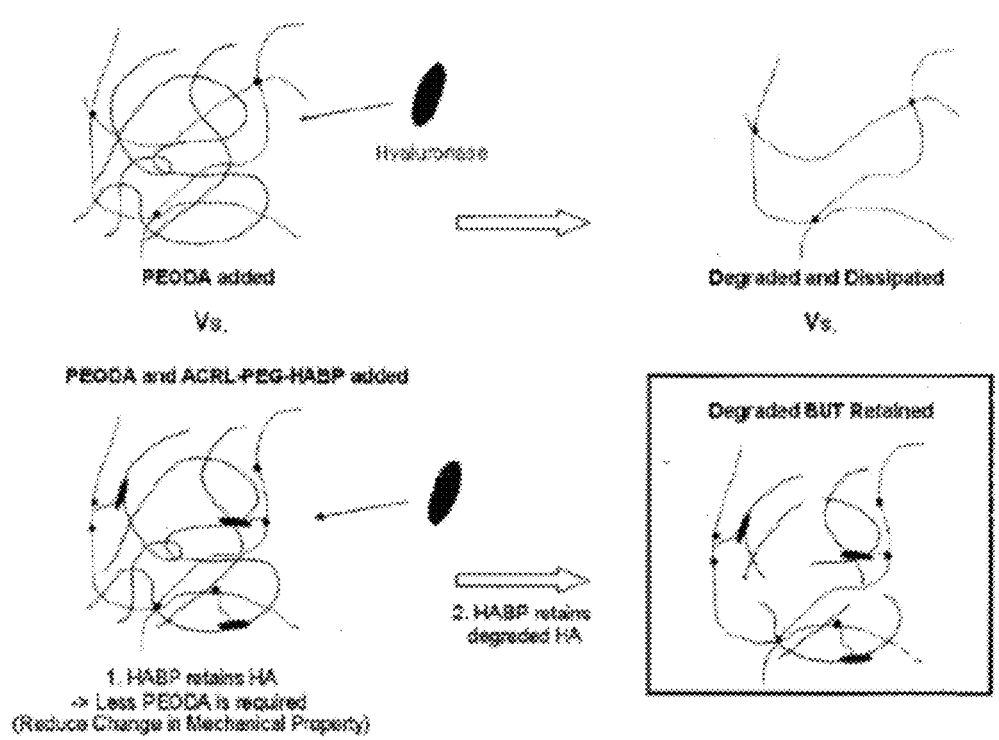
FIG. 2 is a schematic depiction showing how HA in prior art PEGDA hydrogels are degraded by hyaluronidase. With HA binding peptide crosslinked to a PEGDA backbone, as in the biomaterials of the present invention, HA can be retained in the PEGDA construct even after the degradation.

The resulting 13c, kinetic and 13d, static friction coefficients were similar to native cartilage samples bathed and tested in HA. Data are mean+/−standard deviation.

DETAILED DESCRIPTION OF THE INVENTION

Biomaterials such as hydrogels based on natural polymers, such as alginate, collagen and hyaluronic acid (HA), are widely used for tissue engineering applications.

In accordance with an embodiment, the present invention provides novel biomaterial compositions which bind HA and which are activated by visible light that comprise a crosslinkable polymeric material or functional derivatives thereof. The polymers and derivatized polymeric materials may be further described as containing modified reactive groups that facilitate polymerization, attachment and cross-linking of the polymeric material on exposure to light. By exposure to visible light, the liquid form of the synthetic polymer hydrogel in the preparation takes on a semisolid or gel form, and is amenable to desired contouring and manipulation to result in a desired, solid and/or semisolid polymerized form in situ. The inventive technology is useful for engineering tissue with many cell types, such as stem cells, adipose derived stem cells, chondrocytes, and including, for example, human mesenchymal stem cells (hMSCs).

As used herein, "biocompatible biomaterial" are materials that can be used for tissue reconstruction or cosmetic procedures that are acceptable for use in a mammal, preferably in a human subject.

In accordance with an embodiment, the present invention provides a biomaterial comprising at least one biologically compatible polymer having one or more HA binding peptides covalently linked to the biologically compatible polymer, and at least one other component.

In accordance with a further embodiment, the biomaterials described herein can include those wherein the at least one other component is selected from the group consisting of oligomers, polymers, biosynthetic proteins or peptides, naturally occurring peptides or proteins, processed naturally occurring peptides or proteins, and polysaccharides.

In accordance with an embodiment, the present invention provides a hydrogel composition comprising: a) one or more first biocompatible polymers having one or more HA binding peptides (HABPep) which are covalently linked to the first biocompatible polymers; and b) one or more second biocompatible polymers; wherein the biocompatible polymers of a) and b) are cross linked together to form a hydrogel.

As disclosed herein, virtually any polymeric material that may be modified to include a light-activated derivatized reactive group may be used in the preparation of the present novel HA binding hydrogel compositions. By way of example, and not limitation, and in particular embodiments, the polymer can comprise synthetic reactants and comprises poly(ethylene glycol) (PEG) or a derivative thereof. In some embodiments, the polymer derivative comprises poly(ethylene oxide) diacrylate (PEODA) or polyethylene glycol) diacrylate (PEGDA).

In accordance with an embodiment, the one or more first biocompatible polymers can be PEG or a derivative thereof.

In accordance with another embodiment, the one or more second biocompatible polymers can be PEODA or a derivative thereof.

In accordance with a further embodiment, the one or more first and second biocompatible polymers can be hydrophilic.

In accordance with still another embodiment, the one or more first or second biocompatible polymers are selected from the group consisting of: Poly(ethylene glycol), Poly (propylene glycol), Poly(methyl vinyl ether), Oligoethylene, Poly(isobutylene) Poly(tetrahydrofuran) Poly(oxytrimethylene), Poly(dimethylsiloxsane), Poly(dimethylsilane), Nylon 6, Nylon 11, Poly(acrylonitrile), Squalane, Poly(1,3-dioxolane), Poly(iminooligomethylene), Poly(l-lysine), Polyethyleneimine, Poly(adipate), Poly(l-caprolactone), Poly(L-lactic acid), or derivatives thereof.

In accordance with another embodiment, the one or more first or second biocompatible polymers are mono, or disubstituted with an acrylate group.

In accordance with an embodiment, the HABPep is a peptide which is capable of specifically binding HA. Many such HA binding peptides are known in the art. See for example WO/2006/130974, which describes many such peptides which have at least one repetition of the amino acid residue sequence $B_1X_7-B_2$ where B is any basic amino acid residue and $X_7$ are any 7 non-acidic amino acid residues. The binding of the peptide to HA may be enhanced by the addition of basic amino acid residues between B1 and B2 or flanking either end of motif (non-conservative substitutions). Another peptide isolated by phage display, HABP52, has been shown to bind to hyaluronic acid (HA) with high affinity and to inhibit leukocyte adhesion to HA as described in U.S. Pat. No. 6,653,285. These peptides lack similarity to the HA binding motifs discussed above. HABP52 inhibits contact hypersensitivity responses in mice by blocking skin-directed trafficking of inflammatory leukocytes.

The HABP52 family of HA binding peptides includes peptides with an amino acid sequence selected from the group consisting of i) (GAHWQFNALTVR) (SEQ ID NO: 1) or (CRRDDGAHWQFNALTVR) (SEQ ID NO: 2) or a conservative amino acid substitution thereof at a residue position other than 4, 5, 6, 9, 10 or 11, ii) Gly-Ala-Ala-Trp-Gln-Phe-Asn-Ala-Leu-Thr-Val-Arg (SEQ ID NO: 3) or a conservative amino acid substitution thereof at a residue position other than 4, 5, 6, 9, 10 or 11, iii) Gly-Ala-His-Trp-Gln-Phe-Ala-Ala-Leu-Thr-Val-Arg (SEQ ID NO: 4) or a conservative amino acid substitution thereof at a residue position other than 4, 5, 6, 9, 10 or 11, and iv) Gly-Ala-His-Trp-Gln-Phe-Asn-Ala-Leu-Thr-Val-Ala (SEQ ID NO: 5) or a conservative amino acid substitution thereof at a residue position other than 4, 5, 6, 9, 10 or 11.

In alternative embodiments, different chemical functional groups may be chosen for the desired cell response, tissue development or scaffold properties.

By "hydrogel" is meant a water-swellable polymeric matrix that can absorb water to form elastic gels, wherein "matrices" are three-dimensional networks of macromolecules held together by covalent or noncovalent crosslinks. On placement in an aqueous environment, dry hydrogels swell by the acquisition of liquid therein to the extent allowed by the degree of cross-linking.

A biologically compatible polymer refers to a polymer which is functionalized to serve as a composition for creating an implant. The polymer is one that is a naturally occurring polymer or one that is not toxic to the host. The polymer can, e.g., contain at least an imide. The polymer may be a homopolymer where all monomers are the same or a hetereopolymer containing two or more kinds of monomers. The terms "biocompatible polymer," "biocompatible cross-linked polymer matrix" and "biocompatibility" when used in relation to the instant polymers are art-recognized are considered equivalent to one another, including to biologically compatible polymer. For example, biocompatible polymers include polymers that are neither toxic to the host (e.g., an animal or human), nor degrade (if the polymer degrades at a rate that produces monomeric or oligomeric subunits or other byproducts at toxic concentrations in the host).

Polymer is used to refer to molecules composed of repeating monomer units, including homopolymers, block copolymers, heteropolymers, random copolymers, graft copolymers and so on. "Polymers" also include linear polymers as well as branched polymers, with branched polymers including highly branched, dendritic, and star polymers.

A monomer is the basic repeating unit in a polymer. A monomer may itself be a monomer or may be dimer or oligomer of at least two different monomers, and each dimer or oligomer is repeated in a polymer.

A polymerizing initiator refers to any substance that can initiate polymerization of monomers or macromers by, for example, free radical generation. The polymerizing initiator often is an oxidizing agent. Exemplary polymerization initiators include those which are activated by exposure to, for example, electromagnetic radiation or heat.

In accordance with another embodiment, the present invention provides for a method for forming an implant in vivo. In particular embodiments, the method comprises administering a liquid derivatized monomeric material into a desired site in a host, inducing gelation to form a polymeric material by exposing said liquid derivatized monomeric material to light, and contouring said gelling and gelled polymeric material into a desired conformation to provide an implant.

An "active agent" and a "biologically active agent" are phrases used interchangeably herein to refer a chemical or biological compound that induces a desired pharmacological or physiological effect, wherein the effect may be prophylactic or therapeutic. The terms also encompass pharmaceutically acceptable, pharmacologically active derivatives of those active agents specifically mentioned herein, including, but not limited to, salts, esters, amides, prodrugs, active metabolites, analogs and the like.

When the terms "active agent," "pharmacologically active agent" and "drug" are used, it is to be understood that the invention includes the active agent per se, as well as pharmaceutically acceptable, pharmacologically active salts, esters, amides, prodrugs, metabolites, analogs etc. The active agent can be a biological entity, such as a virus or cell, whether naturally occurring or manipulated, such as transformed.

The term "crosslinked" as used herein refers to a composition containing intermolecular links and, optionally, intramolecular links, arising from the formation of covalent bonds. Covalent bonding between two crosslinkable components may be direct, in which case, an atom in one component is directly bound to an atom in the other component, or it may be indirect, that is, for example, through a linking group. A crosslinked gel or polymer matrix may, in addition to covalent bonds, also include intermolecular and/or intramolecular noncovalent bonds such as hydrogen bonds and electrostatic (ionic) bonds.

The term "functionalized" as used herein, refers to a modification of an existing molecular segment to generate or introduce a new reactive or more reactive group (e.g., an amine, ester or imide group) that is capable of undergoing reaction with another molecule, polymer or functional group (e.g., an amine, an ester or a carboxyl group) to form a covalent bond. For example, carboxylic acid groups can be functionalized by reaction with a carbodiimide and an imide reagent using known procedures to provide a new reactive functional group in the form of an imide group substituting for the hydrogen in the hydroxyl group of the carboxyl function.

The term "gel" refers to a state of matter between liquid and solid, and is generally defined as a polymer network swollen in a liquid medium. Typically, a gel is a two-phase colloidal dispersion containing both solid and liquid, wherein the amount of solid is greater than that in the two-phase colloidal dispersion referred to as a "sol." As such, a "gel" has some of the properties of a liquid (i.e., the shape is resilient and deformable) and some of the properties of a solid (i.e., the shape is discrete enough to maintain three dimensions on a two-dimensional surface). "Gelation time," also referred to herein as "gel time," refers to the time it takes for a composition to become non-flowable under modest stress. This is generally exhibited as reaching a physical state in which the elastic modulus, $G'$, equals or exceeds the viscous modulus, $G''$, i.e., when tan (A) becomes 1 (as may be determined using conventional rheological techniques).

A gel that is "moldable" is one that is conformable to a shape before or during exposure to the light, and which can be contoured or shaped to assume and to retain a particular shape. Thus, following instillation or administration in a space and illumination to catalyze gelation, a composition of interest can be shaped by external manipulation, using, for example, a shaping means, such as, a surgical depressor or other tool or instrument with a flat or curved surface, fingers, the palm, a knuckle and so on.

A "matrix" is a three-dimensional network of macromolecules held together by covalent or noncovalent crosslinks. On placement in an aqueous environment, dry hydrogels swell to the extent allowed by the viscosity, the gel state and/or degree of crosslinking in the polymer or network. A matrix can be a network.

Photopolymerization is a method to covalently crosslink polymer chains, whereby a photoinitiator and polymer solution (termed "pre-gel" or monomer solution) are exposed to a light source specific to the photoinitiator. On activation, the photoinitiator reacts with specific functional groups in the polymer chains, linking the functional groups to form the hydrogel. The reaction generally is rapid (3-5 minutes) and can proceed at room or body temperature. Photoinduced gelation enables spatial and temporal control of scaffold formation, permitting shape manipulation after injection and during gelation in vivo. Cells and bioactive factors can be incorporated into the hydrogel scaffold by simply mixing same in and with the polymer solution prior to gelation.

In accordance with an embodiment, the hydrogel compositions of the present invention can be semi-interpenetrating networks that promote cell, tissue and organ repair while discouraging scar formation. The hydrogels of interest can also be derivatized to contain a reactive group to facilitate polymerization and linking.

The terms "substituted," "functional group" and "reactive group" are contemplated to include all permissible substituents of organic compounds on the monomers, polymers and networks of interest. In a broad aspect, the permissible substituents include acyclic and cyclic, branched and unbranched, carbocyclic and heterocyclic, aromatic and nonaromatic substituents of organic compounds. Illustrative substituents include, for example, carboxy groups, amine groups, amide groups, hydroxyl groups and so on, as known in the art. The permissible substituents may be one or more and the same or different for appropriate organic compounds.

A functional group or a moiety capable of mediating formation of a polymer or network can be added to a naturally occurring molecule or a synthetic molecule practicing methods known in the art. Functional groups include the various radicals and chemical entities taught herein, and include alkenyl moieties such as acrylates, methacrylates, dimethacrylates, oligoacrylates, oligomethacrylates, ethacrylates, itaconates or acrylamides.

Further functional groups include aldehydes. Other functional groups may include ethylenically unsaturated monomers including, for example, alkyl esters of acrylic or methacrylic acid such as methyl methacrylate, ethyl methacrylate, butyl methacrylate, ethyl acrylate, butyl acrylate, hexyl acrylate, n-octyl acrylate, lauryl methacrylate, 2-ethylhexyl methacrylate, nonyl acrylate, benzyl methacrylate, the hydroxyalkyl esters of the same acids such as 2-hydroxyethyl acrylate, 2-hydroxyethyl methacrylate, and 2-hydroxypropyl methacrylate, the nitrite and amides of the same acids such as acrylonitrile, methacrylonitrile, and methacrylamide, vinyl acetate, vinyl propionate, vinylidene chloride, vinyl chloride, and vinyl aromatic compounds such as styrene, t-butyl styrene and vinyl toluene, dialkyl maleates, dialkyl itaconates, dialkyl methylene-malonates, isoprene and butadiene. Suitable ethylenically unsaturated monomers containing carboxylic acid groups include acrylic monomers such as acrylic acid, methacrylic acid, ethacrylic acid, itaconic acid, maleic acid, fumaric acid, monoalkyl itaconate including monomethyl itaconate, monoethyl itaconate, and monobutyl itaconate, monoalkyl maleate including monomethyl maleate, monoethyl maleate, and monobutyl maleate, citraconic acid and styrene carboxylic acid. Suitable polyethylenically unsaturated monomers include butadiene, isoprene, allylmethacrylate, diacrylates of alkyl dials such as butanediol diacrylate and hexanediol diacrylate, divinyl benzene and the like.

Suitable hydrophilic polymers to serve as the first or second biocompatible polymer include synthetic polymers such as poly(ethylene glycol), poly(ethylene oxide), partially or fully hydrolyzed poly(vinyl alcohol), poly(vinylpyrrolidone), poly(ethyloxazoline), poly(ethylene oxide)-co-poly(propylene oxide) block copolymers (poloxamers and meroxapols), poloxamines, carboxymethyl cellulose, and hydroxyalkylated celluloses such as hydroxyethyl cellulose and methylhydroxypropyl cellulose, and natural polymers, such as, polysaccharides or carbohydrates such as Ficoll™, polysucrose, dextran, heparan sulfate, chondroitin sulfate or alginate, and polypeptides or proteins such as gelatin, collagen, albumin or ovalbumin, or copolymers or blends thereof.

A variety of photolabile compounds are available, including, but not limited to, disulfides, benzoins and benzyls for use as a photoinitiator of interest. A non-limiting list of exemplary photoinitiators includes benzophenone, trimethylbenzophenone, thioxanthone, 2-chlorothioxanthone, 9,10-anthraquinone, bis-4,4-dimethylaminobenzophenone, benzoin ethers, benzilketals, α-dialkoxyacetophenones, α-hydroxyalkylphenones, α-amino alkylphenones, acylphosphine oxides, benzophenones/amines, thioxanthones/amines, titanocenes, 2,2-dimethoxy acetophenone, 1-hydroxycyclohexyl phenyl ketone, 2-methyl-1-[4-(methylthio) pheny l]-2-(4-morpholinyl)-1-propanone, 2-hydroxy-1-[4-(hydroxyethoxy)phenyl]-2-methyl-1-propanone, α-hydroxy-ketones and benzilidimethyl-ketals, e.g. Irgacure 651 and 184, and Darocur 1173, marketed by Ciba Chemicals, Rose Bengal, camphorquinone, erythrosine, and mixtures thereof, and so on.

The pregel, monomer solution can comprise a photoinitiator in an amount of, for example, 0.05 to about 1.5% by weight, 0.1 to 1.0% by weight or 0.08 to 0.5% by weight, based on the entire polymerizable component to be gelled, the degree of polymerization and/or networking desired, the rate of polymerization and/or networking desired and so on, as a design choice.

The monomer solution can contain the photoinitiator, the photoinitiator can be mixed with the monomer prior to use or applied separately. Optionally, a proton acceptor is included. Suitable such proton acceptors are known in the art. An example of such a suitable proton acceptor is an amine, such as a tertiary amine, such as, triethylamine.

An illuminating means can be a light source suitable for activating the photoinitiator used, and which can activate the photoinitiator from outside of the body. While thermal initiators can be used and thus, an infrared source used, and ultraviolet-activated initiators can be used, and thus, a suitable ultraviolet source used, a preferred light source is a white light source. Thus, a suitable photoinitiator is used, such as Eosin Y, so that the maximum absorption of the initiator and the light source are tuned. As mentioned hereinabove, one such visible light source is an IPL device. A commonly used commercially available IPL carries a xenon flash lamp. Other suitable light sources can be used so long as gelation occurs in the body, at the site, under the skin surface and so on, such as, by applying the electromagnetic radiation to the body, to the site as needed, or from above the tissue surface. The electromagnetic radiation is applied at an intensity, for a time and for a duration that enables gelation. The light source can be situated above the tissue surface or directly on the tissue surface.

The hydrogel composition of the present invention also can contain any of a variety of other materials, such as, inert materials, such as, preservatives, fillers, excipients or diluents.

By way of example, polymer matrix compositions of the invention can be used to block or fill various lumens and voids just below a skin surface. Thus, the instant invention relates to a method of tissue augmentation in a host, such as a human patient, wherein said monomer solution of interest is introduced at a site of interest using methods known in the art, such as injecting a monomer at or in a tissue site in need of augmentation and once applied, exposing the body surface to a visible light to cause polymerization of the deposited monomer solution. A kit containing the injectable monomer, and a delivery means, such as a syringe, as well as an optional light source, a photoinitiator and proton acceptor, is also provided.

In accordance with an embodiment, the present invention provides a method of treating a cartilage defect in a tissue of a subject comprising administering to the tissue of the subject in need of treatment, a therapeutically effective amount of the hydrogel composition described herein.

The term "cartilage defect" as used herein can include any disease or injury induced disruption to the natural cartilage or tissue surface. Examples of such defects include, but are not limited to, damage due to osteo or rheumatoid arthritis, tears, excessive wear of joints due to repetitive use or injury, damage or defects due to other inflammatory or autoimmune diseases.

The term "augmentation" as used herein, means the repair, prevention or alleviation of defects, particularly defects due to loss or absence of tissue, by providing, augmenting, or replacing such tissue with a polymer or network or interest. Augmentation is also meant to include supplementation of a natural structure or feature, that is, a building of adding to an existing body part, for example, to increase the size thereof, such a lips, nose, breast, ears, portions of the reproductive organs, eyebrows, chin, cheeks and so on. While the invention is designed primarily for soft tissue augmentation, hard tissue augmentation is encompassed as the injectable compositions of the invention can be applied to a hard tissue and can be used in combination with, for example, materials to promote mineralization or bone formation. Thus, tissue augmentation can include the filling of lines, folds, wrinkles, minor facial depressions, cleft lips, superficial wrinkles and the like, such as, in the face and neck; the correction of minor deformities due to aging or disease, including in the hands and feet, fingers and toes; the augmentation of the vocal cords or glottis to rehabilitate speech; the dermal filling of sleep lines and expression lines; the replacement of dermal and subcutaneous tissue lost due to aging; the augmentation of lips; the filling of wrinkles and the orbital groove around the eye; the augmentation of the breast; the augmentation of the chin; the augmentation of the cheek and/or nose; the filling of indentations in soft tissue, dermal or subcutaneous, due to, e.g., overzealous liposuction or other trauma; the filling of acne or traumatic scars and rhytids; the filling of nasolabial lines, nasoglabellar lines and infraoral lines and so on.

"Incorporated," "encapsulated," and "entrapped" are art-recognized when used in reference to a therapeutic agent, dye, or other material and a polymeric composition, such as a composition of the present invention. In certain embodiments, these terms include incorporating, formulating or otherwise including such agent into a composition that allows for sustained release of such agent in the desired application. The terms may contemplate any manner by which a therapeutic agent or other material is incorporated into a polymer matrix, including, for example, attached to a monomer of such polymer (by covalent or other binding interaction) and having such monomer be part of the polymerization to give a polymeric formulation, distributed throughout the polymeric matrix, appended to the surface of the polymeric matrix (by covalent or other binding interactions), encapsulated inside the polymeric matrix, etc. The term "co-incorporation" or "co-encapsulation" refers to the incorporation of a therapeutic agent or other material and at least one other therapeutic agent or other material in a subject composition.

More specifically, the physical form in which any therapeutic agent or other material is encapsulated in polymers may vary with the particular embodiment. For example, a therapeutic agent or other material may be first encapsulated in a microsphere and then combined with the polymer in such a way that at least a portion of the microsphere structure is maintained. Alternatively, a therapeutic agent or other material may be sufficiently immiscible in the polymer of the invention that it is dispersed as small droplets, rather than being dissolved in the polymer. Any form of encapsulation or incorporation is contemplated by the present invention, in so much as the sustained release of any encapsulated therapeutic agent or other material determines whether the form of encapsulation is sufficiently acceptable for any particular use.

Pharmaceutically acceptable salts are art-recognized, and include relatively non-toxic, inorganic and organic acid addition salts of compositions of the present invention, including without limitation, therapeutic agents, excipients, other materials and the like. Examples of pharmaceutically acceptable salts include those derived from mineral acids, such as hydrochloric acid and sulfuric acid, and those derived from organic acids, such as ethanesulfonic acid, benzenesulfonic acid, p-toluenesulfonic acid, and the like. Examples of suitable inorganic bases for the formation of salts include the hydroxides, carbonates, and bicarbonates of ammonia, sodium, lithium, potassium, calcium, magnesium, aluminum, zinc and the like. Salts may also be formed with suitable organic bases, including those that are non-toxic and strong enough to form such salts. For purposes of illustration, the class of such organic bases may include mono-, di-, and trialkylamines, such as methylamine, dimethylamine, and triethylamine; mono-, di-, or trihydroxyalkylamines such as mono-, di-, and triethanolamine; amino acids, such as arginine and lysine; guanidine; N-methylglucosamine; N-methylglucamine; L-glutamine; N-methylpiperazine; morpholine; ethylenediamine; N-benzylphenthylamine; (trihydroxymethyl) aminoethane; and the like, see, for example, J. Pharm. Sci., 66: 1-19 (1977).

In one aspect of this invention, a composition comprising a cross-linked polymer matrix or gel and one or more biologically active agents may be prepared. The biologically active agent may vary widely with the intended purpose for the composition. The term active is art-recognized and refers to any moiety that is a biologically, physiologically, or pharmacologically active substance that acts locally or systemically in a subject. Examples of biologically active agents, that may be referred to as "drugs", are described in well-known literature references such as the Merck Index, the Physicians' Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a biologically active agent may be used which are capable of being released the subject composition, for example, into adjacent tissues or fluids upon administration to a subject. In some embodiments, a biologically active agent may be used in cross-linked polymer matrix of this invention, to, for example, promote cartilage formation. In other embodiments, a biologically active agent may be used in cross-linked polymer matrix of this invention, to treat, ameliorate, inhibit, or prevent a disease or symptom, in conjunction with, for example, promoting cartilage formation.

Further examples of biologically active agents include, without limitation, enzymes, receptor antagonists or agonists, hormones, growth factors, autogenous bone marrow, antibiotics, antimicrobial agents, and antibodies. The term "biologically active agent" is also intended to encompass various cell types and genes that can be incorporated into the compositions of the invention.

In certain embodiments, the subject compositions comprise about 1% to about 75% or more by weight of the total composition, alternatively about 2.5%, 5%, 10%, 20%, 30%, 40%, 50%, 60% or 70%, of a biologically active agent.

Non-limiting examples of biologically active agents include following: adrenergic blocking agents, anabolic agents, androgenic steroids, antacids, anti-asthmatic agents, anti-allergenic materials, anti-cholesterolemic and anti-lipid agents, anti-cholinergics and sympathomimetics, anti-coagulants, anti-convulsants, anti-diarrheal, anti-emetics, anti-hypertensive agents, anti-infective agents, anti-inflammatory agents such as steroids, nonsteroidal anti-inflammatory agents, anti-malarials, anti-manic agents, anti-nauseants, antineoplastic agents, anti-obesity agents, anti-parkinsonian agents, anti-pyretic and analgesic agents, anti-spasmodic agents, anti-thrombotic agents, anti-uricemic agents, antianginal agents, antihistamines, anti-tussives, appetite suppressants, benzophenanthridine alkaloids, biologicals, cardioactive agents, cerebral dilators, coronary dilators, decongestants, diuretics, diagnostic agents, erythropoietic agents, estrogens, expectorants, gastrointestinal sedatives, hyperglycemic agents, hypnotics, hypoglycemic agents, ion exchange resins, laxatives, mineral supplements, mitotics, mucolytic agents, growth factors, neuromuscular drugs, nutritional substances, peripheral vasodilators, progestational agents, prostaglandins, psychic energizers, psychotropics, sedatives, stimulants, thyroid and anti-thyroid agents, tranquilizers, uterine relaxants, vitamins, antigenic materials, and prodrugs.

Specific examples of useful biologically active agents the above categories include: (a) anti-neoplastics such as androgen inhibitors, antimetabolites, cytotoxic agents, and immunomodulators; (b) anti-tussives such as dextromethorphan, hydrobromide, noscapine, carbetapentane citrate, and chlophedianol hydrochloride; (c) antihistamines such as chlorpheniramine phenindamine tartrate, pyrilamine doxylamine succinate, and phenyltoloxamine citrate; (d) decongestants such as hydrochloride, phenylpropanolamine hydrochloride, pseudoephedrine hydrochloride, and ephedrine; (e) various alkaloids such as codeine phosphate, codeine sulfate, and morphine; (f) mineral supplements such as potassium chloride, zinc chloride, calcium carbonate, magnesium oxide, and other alkali metal and alkaline earth metal salts; (g) ion exchange resins such as such as N-acetyl-procainamide; (i) antipyretics and analgesics such as acetaminophen, aspirin and ibuprofen; appetite suppressants such as phenyl-propanol amine or caffeine; (k) expectorants such as guaifenesin; (l) antacids such as aluminum hydroxide and magnesium hydroxide; biologicals such as peptides, polypeptides, proteins and amino acids, hormones, interferons or cytokines and other bioactive peptidic compounds, such as calcitonin, ANF, EPO and insulin; (n) anti-infective agents such as anti-fungals, anti-virals, antiseptics and antibiotics; and (m) desensitizing agents and antigenic materials, such as those useful for vaccine applications.

More specifically, non-limiting examples of useful biologically active agents include the following therapeutic categories: analgesics, such as nonsteroidal anti-inflammatory drugs, opiate agonists and salicylates; antihistamines, such as H1-blockers and H2-blockers; anti-infective agents, such as antihelmintics, antianaerobics, antibiotics, aminoglycoside antibiotics, antifungal antibiotics, cephalosporin antibiotics, macrolide antibiotics, miscellaneous antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, such as alkylating agents, nitrogen mustard alkylating agents, nitrosourea alkylating agents, antimetabolites, purine analog antimetabolites, pyrimidine analog antimetabolites, hormonal antineoplastics, natural antineoplastics, antibiotic natural antineoplastics, and *vinca* alkaloid natural antineoplastics; autonomic agents, such as anticholinergics, antimuscarinic anticholinergics, ergot alkaloids, parasympathomimetics, cholinergic agonist parasympathomimetics, cholinesterase inhibitor parasympathomimetics, sympatholytics, a-blocker sympatholytics, sympatholytics, sympathomimetics, and adrenergic agonist sympathomimetics; cardiovascular agents, such as antianginals, antianginals, calcium-channel blocker antianginals, nitrate antianginals, antiarrhythmics, cardiac glycoside antiarrhythmics, class I antiarrhythmics, class antiarrhythmics, class antiarrhythmics, class IV antiarrhythmics, antihypertensive agents, a-blocker antihypertensives, angiotensin-converting enzyme inhibitor (ACE inhibitor) antihypertensives, 13-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, reductase inhibitor antilipemics, inotropes, cardiac glycoside inotropes, and thrombolytic agents; dermatological agents, such as antihistamines, anti-inflammatory agents, corticosteroid anti-inflammatory agents, anesthetics, topical anti-infectives, topical anti-infectives, antiviral topical anti-infectives, and topical antineoplastics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2-blocker anti-ulcer agents, cholelitholytic agents, digestants, emetics, laxatives and stool softeners, and prokinetic agents; general anesthetics, such as inhalation anesthetics, halogenated inhalation anesthetics, intravenous anesthetics, barbiturate intravenous anesthetics, benzodiazepine intravenous anesthetics, and opiate agonist intravenous anesthetics; hematological agents, such as antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, such as abortifacients, adrenal agents, corticosteroid adrenal agents, androgens, anti-androgens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, gold compound anti-inflammatory agents, immunosuppressive anti-inflammatory agents, nonsteroidal anti-inflammatory drugs, salicylate anti-inflammatory agents, skeletal muscle relaxants, neuromuscular blocker skeletal muscle relaxants, and reverse neuromuscular blocker skeletal muscle relaxants; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, anti-glaucoma agents, mitotics, anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs; psychotropic agents, such as antidepressants, heterocyclic antidepressants, monoamine oxidase inhibitors selective serotonin re-uptake inhibitors tricyclic antidepressants, antimanics, anti psychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory antiinflammatory agents, and respiratory corticosteroid anti-inflammatory agents; toxicology agents, such as antidotes, heavy agents, substance abuse agents, deterrent substance abuse agents, and withdrawal substance abuse agents; minerals; and vitamins, such as vitamin A, vitamin B, vitamin C, vitamin D, vitamin E, and vitamin K.

Other classes of biologically active agents from the above categories include: (1) analgesics in general, such as lidocaine, other "caine" analgesics or derivatives thereof, and nonsteroidal anti-inflammatory drugs inflammatory (NSAIDs) analgesics, including diclofenac, ibuprofen, ketoprofen, and naproxen; (2) opiate agonist analgesics, such as codeine, fentanyl, hydromorphone, and morphine; (3) salicylate analgesics, such as aspirin (ASA) (enteric coated ASA); (4) H1-blocker antihistamines, such as clemastine and terfenadine; (5) H2-blocker antihistamines, such as cimetidine, famotidine, nizadine, and ranitidine; (6) antiinfective agents, such as mupirocin; (7) antianaerobic antiinfectives, such as chloramphenicol and clindarnycin; (8) antifungal antibiotic anti-infectives, such as amphotericin b, clotrimazole, fluconazole, and ketoconazole; (9) macrolide antibiotic anti-infectives, such as azithromycin and erythromycin; (10) miscellaneous antibiotic anti-infectives, such as and imipenem; penicillin, (11) antibiotic anti-infectives, such as nafcillin, oxacillin, penicillin G, and penicillin V; (12) quinolone antibiotic anti-infectives, such as ciprofloxacin and nortfloxacin; (13) tetracycline antibiotic anti-infectives, such as doxycycline, minocycline and tetracycline; (14) antituberculosis antimycobacterial anti-infectives such as isoniazid and rifampin; (15) anti-protozoal anti-infectives, such as atovaquone and dapsone; (16) antimalarial anti protozoal anti-infectives, such as chloroquine and pyrimethamine; (17) anti-retroviral anti-infectives, such as ritonavir and zidovudine; (18) antiviral anti-infective agents, such as acyclovir, ganciclovir, interferon-γ, and rimantadine; (19) alkylating antineoplastic agents, such as carboplatin and cisplatin; (20) nitrosourea alkylating antineoplastic agents, such as carmustine (BCNU); (21) antimetabolite antineoplastic agents, such as methotrexate; (22) pyrimidine analog antineoplastic agents, such as fluorouracil (S-FU) and gemcitabine; (23) hormonal antineoplastics, such as goserelin, leuprolide, and tamoxifen; (24) natural antineoplastics, such as aldesleukin, interleukin-2, docetaxel, etoposide, interferon; paclitaxel, other taxane derivatives, and tretinoin (ATRA); (25) antibiotic natural antineoplastics, such as bleomycin, dactinomycin, daunorubicin, doxorubicin, and mitomycin; (26) vinca alkaloid natural antineoplastics, such as vinblastine and vincristine; (27) autonomic agents, such as nicotine; (28) anticholinergic autonomic agents, such as benztropine and trihexyphenidyl; (29) antimuscarinic anticholinergic autonomic agents, such as atropine and oxybutynin; (30) ergot alkaloid autonomic agents, such as bromocriptine; (31) cholinergic agonist parasympathomimetics, such as pilocarpine; (32) cholinesterase inhibitor parasympathomimetics, such as pyridostigmine; (33) a-blocker sympatholytics, such as prazosin; (34) D-blocker sympatholytics, such as atenolol; (35) adrenergic sympathomimetics, such as albuterol and dobutamine; (36) cardiovascular agents, such as aspirin (ASA) (enteric coated ASA); (37) D-blocker antianginals, such as atenolol and propranolol; (38) calcium-channel blocker antianginals, such as nifedipine and verapamil; (39) nitrate antianginals, such as isosorbide dinitrate (ISDN); (40) cardiac glycoside antiarrhythmics, such as (41) class I antiarrhythmics, such as lidocaine, mexiletine, phenytoin, procainamide, and quinidine; (42) class antiarrhythmics II, such as atenolol, metoprolol, propranolol, and timolol; (43) class III antiarrhythmics, such as amiodarone; (44) class IV antiarrhythmics, such as diltiazem and verapamil; (45) antihypertensives, such as prazosin; (46) angiotensin-converting enzyme inhibitor (ACE inhibitor) antihypertensives, such as captopril and enalapril; (47) antihypertensives, such as atenolol, metoprolol, nadolol, and propanolol; (48) calcium-channel blocker antihypertensive agents, such as diltiazem and nifedipine; (49) central-acting adrenergic antihypertensives, such as clonidine and methyldopa; (50) diuretic antihypertensive agents, such as amiloride, furosemide, hydrochlorothiazide (HCTZ), and spironolactone; (51) peripheral vasodilator antihypertensives, such as minoxidil; (52) antilipemics, such as gemfibrozil and probucol; (53) bile acid sequestrant antilipemics, such as cholestyramine; (54) reductase inhibitor antilipemics, such as lovastatin and pravastatin; (55) inotropes, such as amrinone, dobutamine, and dopamine; (56) cardiac glycoside inotropes, such as (57) thrombolytic agents, such as alteplase, anistreplase, streptokinase, and urokinase; (58) dermatological agents, such as colchicine, isotretinoin, methotrexate, minoxidil, tretinoin (59) dermatological corticosteroid anti-inflammatory agents, such as betamethasone and dexamethasone; (60) antifungal topical anti-infectives, such as amphotericin clotrimazole, miconazole, and nystatin; (61) antiviral topical anti-infectives, such as acyclovir; (62) topical antineoplastics, such as (63) electrolytic and renal agents, such as lactulose; (64) loop diuretics, such as furosemide; (65) potassium-sparing diuretics, such as triamterene; (66) thiazide diuretics, such as hydrochlorothiazide (HCTZ); (67) uricosuric agents, such as probenecid; (68) enzymes and (69) thrombolytic enzymes, such as alteplase, anistreplase, streptokinase and urokinase; (70) antiemetics, such as prochlorperazine; (71) salicylate gastrointestinal anti-inflammatory agents, such as sulfasalazine; (72) gastric acid-pump inhibitor anti-ulcer agents, such as omeprazole; (73) H2-blocker anti-ulcer agents, such as cimetidine, famotidine, nizatidine, ranitidine; (74) digestants, such as pancrelipase; (75) prokinetic agents, such as erythromycin; (76) opiate agonist intravenous anesthetics such as fentanyl; (77) hematopoietic antianemia agents, such as (G-CSF), and (GM-CSF); (78) coagulation agents, such as factors 1-10 (A1IF 1-10); (79) anticoagulants, such as warfarin; (80) thrombolytic enzyme coagulation agents, such as alteplase, anistreplase, streptokinase and urokinase; (81) hormones and hormone modifiers, such as bromocriptine; (82) abortifacients, such as methotrexate; (83) antidiabetic agents, such as insulin; (84) oral contraceptives, such as estrogen and progestin; (85) progestin contraceptives, such as levonorgestrel and norgestrel; (86) estrogens such as conjugated estrogens, diethylstilbestrol (DES), estrogen (estradiol, estrone, and estropipate); (87) fertility agents, such as clomiphene, human chorionic gonadotropin (HCG), and menotropins; (88) parathyroid agents such as calcitonin; (89) pituitary hormones, such as desmopressin, goserelin, oxytocin, and vasopressin (ADH); (90) progestins, such as medroxyprogesterone, norethindrone, and progesterone; (91) thyroid hormones, such as levothyroxine; (92) immunobiologic agents, such as interferon beta-1b and interferon gamma-1b; (93) immunoglobulins, such as immune globulin 1M, IMIG, IGIM and immune globulin IVIG; (94) amide local anesthetics, as lidocaine; (95) ester local anesthetics, such as benzocaine and procaine; (96) musculoskeletal corticosteroid anti-inflammatory agents, such as beclomethasone, betamethasone, cortisone, dexamethasone, hydrocortisone, and prednisone; (97) musculoskeletal anti-inflammatory immunosuppressives, such as azathioprine, cyclophosphamide, and methotrexate; (98) musculoskeletal nonsteroidal anti-inflammatory drugs such as diclofenac, ibuprofen, ketoprofen, ketorlac, and naproxen; (99) skeletal muscle relaxants, such as and diazepam; (100) reverse neuromuscular blocker skeletal muscle relaxants, such as pyridostigmine; (101) neurological agents, such as nimodipine, riluzole, tacrine and ticlopidine; (102) anticonvulsants, such as carbamazepine, gabapentin, lamotrigine, phenytoin, and valproic acid; (103) barbiturate anticonvulsants, such as phenobarbital and primidone; (104) benzodiazepine anticonvulsants, such as clonazepam, diazepam, and lorazepam; (105) anti-agents, such as bromocriptine, levodopa, carbidopa, and pergolide; (106) anti-vertigo agents, such as meclizine; (107) opiate agonists, such as codeine, fentanyl, hydromorphone, methadone, and morphine; (108) opiate antagonists, such as naloxone; (109) anti-glaucoma agents, such as timolol; (110) mitotic anti-glaucoma agents, such as pilocarpine; (111) ophthalmic aminoglycoside anti-infectives, such as gentamicin, neomycin, and tobramycin; (112) ophthalmic quinolone anti-infectives, such as ciprofloxacin, norfloxacin, and ofloxacin; (113) ophthalmic corticosteroid anti-agents, such as dexamethasone and prednisolone; (114) ophthalmic nonsteroidal anti-inflammatory drugs such as diclofenac; (115) antipsychotics, such as clozapine, haloperidol, and risperidone; (116) benzodiazepine anxiolytics, sedatives and hypnotics, such as clonazepam, diazepam, lorazepam, oxazepam, and prazepam; (117) psychostimulants, such as methylphenidate and pemoline; (118) such as codeine; (119) bronchodilators, such as (120) adrenergic agonist bronchodilators, such as albuterol; (121) respiratory corticosteroid anti-inflammatory agents, such as dexamethasone; (122) antidotes, such as flumazenil and naloxone; (123) heavy metal agents, such as penicillamine; (124) deterrent substance abuse agents, such as disulfiram, naltrexone, and nicotine; (125) withdrawal substance abuse agents, such as bromocriptine; (126) minerals, such as iron, calcium, and magnesium; (127) vitamin B compounds, such as cyanocobalamin (vitamin B12) and niacin (vitamin B3); (128) vitamin C compounds, such as ascorbic acid; and (129) vitamin D such as calcitriol.

Further, recombinant or cell-derived proteins may be used, such as recombinant beta-glucan; bovine immunoglobulin concentrate; bovine superoxide dismutase; formulation comprising fluorouracil, epinephrine, and bovine collagen; recombinant hirudin (r-Hir), HIV-1 immunogen; recombinant human growth hormone recombinant EPO (r-EPO); gene-activated EPO (GA-EPO); recombinant human hemoglobin (r-Hb); recombinant human mecasermin (r-1GF-1); recombinant interferon α; lenograstim (G-CSF); olanzapine; recombinant thyroid stimulating hormone (r-TSH); and topotecan.

Still further, the following listing of peptides, proteins, and other large molecules may also be used, such as interleukins 1 through 18, including mutants and analogues; interferons a, y, and which may be useful for cartilage regeneration, hormone releasing hormone (LHRH) and analogues, gonadotropin releasing hormone transforming growth factor (TGF); fibroblast growth factor (FGF); tumor necrosis factor-α; nerve growth factor (NGF); growth hormone releasing factor (GHRF), epidermal growth factor (EGF), connective tissue activated osteogenic factors, fibroblast growth factor homologous factor (FGFHF); hepatocyte growth factor (HGF); insulin growth factor (IGF); invasion inhibiting factor-2 (IIF-2); bone morphogenetic proteins 1-7 (BMP 1-7); somatostatin; thymosin-a-y-globulin; superoxide dismutase (SOD); and complement factors, and biologically active analogs, fragments, and derivatives of such factors, for example, growth factors.

Members of the transforming growth factor (TGF) supergene family, which are multifunctional regulatory proteins, may be incorporated in a polymer matrix of the present invention. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (1GF)), (for example, Inhibin A, Inhibin B), growth differentiating factors (for example, GDF-1); and Activins (for example, Activin A, Activin B, Activin AB). Growth factors can be isolated from native or natural sources, such as from mammalian cells, or can be prepared synthetically, such as by recombinant DNA techniques or by various chemical processes. In addition, analogs, fragments, or derivatives of these factors can be used, provided that they exhibit at least some of the biological activity of the native molecule. For example, analogs can be prepared by expression of genes altered by site-specific mutagenesis or other genetic engineering techniques.

Various forms of the biologically active agents may be used. These include, without limitation, such forms as uncharged molecules, molecular complexes, salts, ethers, esters, amides, prodrug forms and the like, which are biologically activated when implanted, injected or otherwise placed into a subject.

In certain embodiments, other materials may be incorporated into subject compositions in addition to one or more biologically active agents. For example, plasticizers and stabilizing agents known in the art may be incorporated in compositions of the present invention. In certain embodiments, additives such as plasticizers and stabilizing agents are selected for their biocompatibility or for the resulting physical properties of the reagents, the setting or gelling matrix or the set or gelled matrix.

Buffers, acids and bases may be incorporated in the compositions to adjust pH. Agents to increase the diffusion distance of agents released from the composition may also be included.

The charge, lipophilicity or hydrophilicity of a composition may be modified by employing an additive. For example, surfactants may be used to enhance miscibility of poorly miscible liquids. Examples of suitable surfactants include dextran, polysorbates and sodium lauryl sulfate. In general, surfactants are used in low concentrations, generally less than about 5%.

The specific method used to formulate the novel formulations described herein is not critical to the present invention and can be selected from a physiological buffer (Feigner et al., U.S. Pat. No. 5,589,466 (1996)).

Therapeutic formulations of the product may be prepared for storage as lyophilized formulations or aqueous solutions by mixing the product having the desired degree of purity with optional pharmaceutically acceptable carriers, diluents, excipients or stabilizers typically employed in the art, i.e., buffering agents, stabilizing agents, preservatives, isotonifiers, non-ionic detergents, antioxidants and other miscellaneous additives, see Remington's Pharmaceutical Sciences, 16th ed., Osol, ed. (1980). Such additives are generally nontoxic to the recipients at the dosages and concentrations employed, hence, the excipients, diluents, carriers and so on are pharmaceutically acceptable.

The compositions can take the form of solutions, suspensions, emulsions, powders, sustained-release formulations, depots and the like. Examples of suitable carriers are described in "Remington's Pharmaceutical Sciences," Martin. Such compositions will contain an effective amount of the biopolymer of interest, preferably in purified form, together with a suitable amount of carrier so as to provide the form for proper administration to the patient. As known in the art, the formulation will be constructed to suit the mode of administration.

Buffering agents help to maintain the pH in the range which approximates physiological conditions. Buffers are preferably present at a concentration ranging from about 2 mM to about 50 mM. Suitable buffering agents for use with the instant invention include both organic and inorganic acids, and salts thereof, such as citrate buffers (e.g., monosodium citrate-disodium citrate mixture, citric acid-trisodium citrate mixture, citric acid-monosodium citrate mixture etc.), succinate buffers (e.g., succinic acid monosodium succinate mixture, succinic acid-sodium hydroxide mixture, succinic acid-disodium succinate mixture etc.), tartrate buffers (e.g., tartaric acid-sodium tartrate mixture, tartaric acid-potassium tartrate mixture, tartaric acid-sodium hydroxide mixture etc.), fumarate buffers (e.g., fumaric acid-monosodium fumarate mixture, fumaric acid-disodium fumarate mixture, monosodium fumarate-disodium fumarate mixture etc.), gluconate buffers (e.g., gluconic acid-sodium glyconate mixture, gluconic acid-sodium hydroxide mixture, gluconic acid-potassium gluconate mixture etc.), oxalate buffers (e.g., oxalic acid-sodium oxalate mixture, oxalic acid-sodium hydroxide mixture, oxalic acid-potassium oxalate mixture etc.), lactate buffers (e.g., lactic acid-sodium lactate mixture, lactic acid-sodium hydroxide mixture, lactic acid-potassium lactate mixture etc.) and acetate buffers (e.g., acetic acid-sodium acetate mixture, acetic acid-sodium hydroxide mixture etc.). Phosphate buffers, carbonate buffers, histidine buffers, trimethylamine salts, such as Tris, HEPES and other such known buffers can be used.

Preservatives may be added to retard microbial growth, and may be added in amounts ranging from 0.2%-1% (w/v). Suitable preservatives for use with the present invention include phenol, benzyl alcohol, m-cresol, octadecyldimethylbenzyl ammonium chloride, benzyaconium halides (e.g., chloride, bromide and iodide), hexamethonium chloride, alkyl parabens, such as, methyl or propyl paraben, catechol, resorcinol, cyclohexanol and 3-pentanol.

Isotonicifiers are present to ensure physiological isotonicity of liquid compositions of the instant invention and include polhydric sugar alcohols, preferably trihydric or higher sugar alcohols, such as glycerin, erythritol, arabitol, xylitol, sorbitol and mannitol. Polyhydric alcohols can be present in an amount of between about 0.1% to about 25%, by weight, preferably 1% to 5% taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols; amino acids, such as arginine, lysine, glycine, glutamine, asparagine, histidine, alanine, ornithine, L-leucine, 2-phenylalanine, glutamic acid, threonine etc.; organic sugars or sugar alcohols, such as lactose, trehalose, stachyose, arabitol, erythritol, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, a-monothioglycerol and sodium thiosulfate; low molecular weight polypeptides (i.e., <10 residues); proteins, such as human serum albumin, bovine serum albumin, gelatin or immunoglobulins; hydrophilic polymers, such as polyvinylpyrrolidone, saccharides, monosaccharides, such as xylose, mannose, fructose or glucose; disaccharides, such as lactose, maltose and sucrose; trisaccharides, such as raffinose; polysaccharides, such as, dextran and so on. Stabilizers can be present in the range from 0.1 to 10,000 w/w per part of biopolymer.

Additional miscellaneous excipients include bulking agents, (e.g., starch), chelating agents (e.g., EDTA), antioxidants (e.g., ascorbic acid, methionine or vitamin E) and cosolvents.

Non-ionic surfactants or detergents (also known as "wetting agents") may be added to help solubilize the therapeutic agent, as well as to protect the therapeutic protein against agitation-induced aggregation, which also permits the formulation to be exposed to shear surface stresses without causing denaturation of the protein. Suitable non-ionic surfactants include polysorbates (20, 80 etc.), polyoxamers (184, 188 etc.), Pluronic® polyols and polyoxyethylene sorbitan monoethers (TWEEN-20®, TWEEN-80® etc.). Non-ionic surfactants may be present in a range of about 0.05 mg/ml to about 1.0 mg/ml, preferably about 0.07 mg/ml to about 0.2 mg/ml.

The present invention provides liquid formulations of a biopolymer having a pH ranging from about 5.0 to about 7.0, or about 5.5 to about 6.5, or about 5.8 to about 6.2, or about 6.0, or about 6.0 to about 7.5, or about 6.5 to about 7.0.

The incubation of the amine-reacting proteoglycan with blood or tissue product can be carried out a specific pH in order to achieve desired properties. E.g., the incubation can be carried out at between a pH of 7.0 and 10.0 (e.g., 7.5, 8.0, 8.5, 9.0, and 9.5). Furthermore, the incubation can be carried out for varying lengths of time in order to achieve the desired properties.

The instant invention encompasses formulations, such as, liquid formulations having stability at temperatures found in a commercial refrigerator and freezer found in the office of a physician or laboratory, such as from about 20° C. to about 5° C., said stability assessed, for example, by microscopic analysis, for storage purposes, such as for about 60 days, for about 120 days, for about 180 days, for about a year, for about 2 years or more. The liquid formulations of the present invention also exhibit stability, as assessed, for example, by particle analysis, at room temperatures, for at least a few hours, such as one hour, two hours or about three hours prior to use.

Examples of diluents include a phosphate buffered saline, buffer for buffering against gastric acid in the bladder, such as citrate buffer (pH 7.4) containing sucrose, bicarbonate buffer (pH 7.4) alone, or bicarbonate buffer (pH 7.4) containing ascorbic acid, lactose, or aspartame. Examples of carriers include proteins, e.g., as found in skim milk, sugars, e.g., sucrose, or polyvinylpyrrolidone. Typically these carriers would be used at a concentration of about 0.1-90% (w/v) but preferably at a range of 1-10%.

The formulations to be used for in vivo administration must be sterile. That can be accomplished, for example, by filtration through sterile filtration membranes. For example, the formulations of the present invention may be sterilized by filtration.

The biopolymer composition will be formulated, dosed and administered in a manner consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the biopolymer to be administered will be governed by such considerations, and can be the minimum amount necessary to prevent, ameliorate or treat a disorder of interest. As used herein, the term "effective amount" is an equivalent phrase refers to the amount of a therapy (e.g., a prophylactic or therapeutic agent), which is sufficient to reduce the severity and/or duration of a disease, ameliorate one or more symptoms thereof, prevent the advancement of a disease or cause regression of a disease, or which is sufficient to result in the prevention of the development, recurrence, onset, or progression of a disease or one or more symptoms thereof, or enhance or improve the prophylactic and/or therapeutic effect(s) of another therapy (e.g., another therapeutic agent) useful for treating a disease. For example, a treatment of interest can increase the use of a joint in a host, based on baseline of the injured or diseases joint, by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. In another embodiment, an effective amount of a therapeutic or a prophylactic agent of interest reduces the symptoms of a disease, such as a symptom of arthritis by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Also used herein as an equivalent is the term, "therapeutically effective amount."

Where necessary, the composition may also include a solubilizing agent and a local anesthetic such as lidocaine or other "caine" anesthetic to ease pain at the site of the injection.

Generally, the ingredients are supplied either separately or mixed together in unit dosage form, for example, as a dry lyophilized powder or water-free concentrate in a sealed container, such as an ampule or sachet indicating the quantity of active agent. Where the composition is to be administered by infusion, it can be dispensed with an infusion bottle containing sterile pharmaceutical grade water or saline. Where the composition is administered by injection, an ampule of sterile water for injection or saline can be provided, for example, in a kit, so that the ingredients may be mixed prior to administration.

An article of manufacture containing materials useful for the treatment of the disorders described above is provided. The article of manufacture comprises a container and a label. Suitable containers include, for example, bottles, vials, syringes and test tubes. The containers may be formed from a variety of materials such as glass or plastic. The container holds a composition which is effective for preventing or treating, for example, a wound or a joint disease and may have a sterile access port (for example, the container may be a vial having a stopper pierceable by a hypodermic injection needle). The label on or associated with the container indicates that the composition is used for treating the condition of choice. The article of manufacture may further comprise a second container comprising a pharmaceutically acceptable buffer, such as phosphate-buffered saline, Ringer's solution and dextrose solution. It may further include other materials desirable from a commercial and user standpoint, including buffers, diluents, filters, needles, syringes and package inserts with instructions for use.

Biologically active agents and other additives may be incorporated into the cross-linked synthetic polymer composition by admixture or added to a reagent preparation. Alternatively, the agents may be incorporated into the cross-linked polymer composition by admixture or added to a reagent preparation. Alternatively, the agents may be incorporated into the cross-linked polymer matrix by binding these agents to the functional groups on the polymers of interest. Such compositions may include linkages that can be easily biodegraded, for example as a result of enzymatic degradation, resulting in the release of the active agent or additive into the target tissue, where it will exert its desired therapeutic effect.

A simple method for incorporating biologically active agents containing nucleophilic groups into the cross-linked polymer composition involves mixing the active agent with a polyelectrophilic component. By varying the relative molar amounts of the different components of the reactive composition, it is possible to alter the net charge of the resulting cross-linked polymer composition, in order to prepare a matrix for the delivery of a charged compound such as a protein or ionizable drug. As such, the delivery of charged proteins or drugs, which would normally diffuse rapidly out of a neutral carrier matrix, can be controlled.

For example, if a molar excess of a component that is polynucleophilic is used, the resulting matrix may have a net positive charge and can be used to ionically bind and deliver negatively charged compounds. Examples of negatively charged compounds that can be delivered from these matrices include various drugs, cells, proteins, and polysaccharides.

If a molar excess of a component that is polyelectrophilic is used, the resulting matrix has a net negative charge and can be used to ionically bind and deliver positively charged compounds. Examples of positively charged compounds that can be delivered from these matrices include various drugs, cells, proteins, and polysaccharides.

The cross-linked polymer matrix compositions of the present invention can also be used to deliver various types of living cells (e.g., a mesenchymal stem cell, a cardiac stem cell, a liver stem cell, a retinal stem cell, and an epidermal stem cell) or genes to a desired site of administration to form new tissue. The term "genes" as used herein is intended to encompass genetic material from natural sources, synthetic nucleic acids, DNA, antisense DNA and RNA.

In accordance with an embodiment, the present invention provides a hydrogel composition as described herein, further comprising one or more living cells.

For example, mesenchymal stem cells can be delivered using polymer matrices to produce cells of the same type as the tissue into which they are delivered. Mesenchymal stem cells may not be differentiated and therefore may differentiate to form various types of new cells due to the presence of an active agent or the effects (chemical, physical, etc.) of the local tissue environment. Examples of mesenchymal stem cells include osteoblasts, chondrocytes, and fibroblasts. For example, osteoblasts can be delivered to the site of a bone defect to produce new bone; chondrocytes can be delivered to the site of a cartilage defect to produce new cartilage; fibroblasts can be delivered to produce collagen wherever new connective tissue is needed; neurectodermal cells can be delivered to form new nerve tissue; epithelial cells can be delivered to form new epithelial tissues, such as liver, pancreas etc.

The cells may be either allogeneic or xenogeneic in origin. The compositions can be used to deliver cells of species that are genetically modified.

In accordance with an embodiment, the present invention provides hydrogel compositions as described herein, wherein the composition further comprises one or more living cells which are selected from the group consisting of a mesenchymal stem cell, a cardiac stem cell, a liver stem cell, a retinal stem cell, and an epidermal stem cell.

In some embodiments, the compositions of the invention may not easily be degraded in vivo. Thus, cells entrapped within the cross-linked polymer matrix compositions will be isolated from the host cells and, as such, will not provoke or will delay an immune response in the host.

To entrap the cells or genes within a cross-linked polymer matrix, the cells or genes may, for example, be premixed with a reagent composition or optionally with a mixture prior to forming a cross-linked polymer matrix, thereby entrapping the cells or genes within the matrix.

In some embodiments, compositions disclosed herein may be positioned in a surgically created defect that is to be reconstructed, and is to be left in that position after the reconstruction has been completed. The present invention may be suitable for use with local tissue reconstructions, pedicle flap reconstructions, corneal flap sealings or free flap reconstructions.

In accordance with an embodiment, the present invention provides a method of filling a void on or in a subject, said method comprising contacting said void with the hydrogel composition of the inventive compositions described herein. In alternative embodiments, the cells used in accordance with the inventive hydrogel compositions can be autologous or allogeneic to the subject receiving the composition.

In accordance with another embodiment, the present invention provides a method of treating a cartilage defect in a tissue of a subject comprising administering to the tissue of the subject in need of treatment, treatment a therapeutically effective amount of the hydrogel compositions described herein. In other embodiments of the invention, the cartilage defects are in joints or ligaments.

In certain embodiments, a polymer of interest can be formed into desired structures, such as films, foams, scaffolds or other three-dimensional structures of interest. In such circumstances, other materials may be incorporated into subject compositions, in addition to one or more biologically active agents. For example, plasticizers and stabilizing agents known in the art may be incorporated in compositions of the present invention. The solid structure can be a component of a kit. Thus, an imidated biologically compatible polymer of interest may be applied to a biological surface as a solid structure and enabled to react with the biological surface. The bridging molecule then can be brought into proximity with the affixed biologically compatible polymer to react therewith.

The compositions disclosed herein may be used in any number of tissue repair applications, such as, but not limited to, seroma and hematoma prevention, skin and muscle flap attachment, repair and prevention of endoleaks, aortic dissection repair, lung volume reduction, neural tube repair, sealing of corneal incisions, reattaching a retina, a wound (e.g., a gunshot wound) and the making of microvascular and neural anastomoses.

In one embodiment, the repair of damaged tissue may be carried out within the context of any standard surgical process allowing access to and repair of the tissue, including open surgery and laparoscopic techniques. Once the damaged tissue is accessed, a composition of the invention is placed in contact with the damaged tissue along with any surgically acceptable patch or implant, if needed.

For example, the hydrogels of the invention can be used to block or fill various lumens and voids in the body of a mammalian subject. The hydrogels can also be used as biosealants to seal fissures or crevices within a tissue or structure (such as a vessel), or junctures between adjacent tissues or structures to prevent leakage of blood or other biological fluids.

The hydrogels can also be used as a large space-filling device for organ displacement in a body cavity during surgical or radiation procedures, for example, to protect the intestines during a planned course of radiation to the pelvis.

The hydrogels of the invention can also be used for augmentation of soft or hard tissue within the body of a mammalian subject. Examples of soft tissue augmentation applications include sphincter (e.g., urinary, anal, esophageal) augmentation and the treatment of rhytids and scars. Examples of hard tissue augmentation applications include the repair and/or replacement of bone and/or cartilaginous tissue.

In accordance with an embodiment, the present invention provides a therapeutic method for the treatment of eye diseases by means of an eye surgery treatment, comprising applying to the eye of a subject in need of such treatment a therapeutically effective amount of the hydrogel compositions described herein. Such surgical procedures include, but are not limited to, corneal transplantation, cataract surgery, glaucoma surgery, and surgery to repair retinal detachment.

In accordance with another embodiment, the present invention provides a therapeutic method for the treatment of dry eye or keratoconjunctivitis sicca (KCS) which can be the result of a number of disorders, including, for example, Sjogren's syndrome. The inventive methods comprise applying the hydrogel compositions of the present invention on the cornea of the eye, and which may include other therapeutic agents, such as estrogens, or cyclosporine.

In accordance with an embodiment, the present invention provides a method for making the hydrogel composition as described herein, comprising: a) obtaining a sufficient amount of one or more first biocompatible polymers in a N-succinamideN-succinimide form in a suitable bicarbonate solution; b) obtaining a sufficient amount of having one or more HA binding peptides (HABPep) in a suitable bicarbonate solution; c) adding the solution of b) to the solution of a) and mixing for a sufficient period of time to produce one or more first biocompatible polymers having one or more HA binding peptides (HABPep) which are covalently linked to the first biocompatible polymers; d) removing unreacted first biocompatible polymers and HABPep; e) purifying the product of c); f) adding a sufficient amount of the product of c) to a solution comprising a sufficient amount second biocompatible polymer in a suitable solvent; g) adding to f) a sufficient amount of a photoinitiating agent; h) exposing the solution of g) to electromagnetic radiation at a sufficient wavelength and intensity to initiate photopolymerization of the solution to produce the hydrogel composition; i) removing the unreacted reagents off) and g) and purify the remaining product of h).

It will be understood by those of ordinary skill that the one or more first biocompatible polymers used in the methods disclosed can include an N-succinamideN-hydroxysuccinimide (NHS) form. For example, the one or more first biocompatible polymer can be Acrylate-PEG-NHS.

Similarly, the one or more second biocompatible polymers used in the methods of the present invention can include PEODA.

In accordance with an embodiment, the present invention provides a bifunctional biopolymer composition comprising a biologically compatible polymer having at least one amine reactive moiety and at least one thiol reactive moiety.

The term "bifunctional biopolymer composition" means a biocompatible polymer which has been chemically modified to have at least one amine reactive moiety and at least one thiol reactive moiety covalently linked to the polymer either directly or via a linking moiety.

In one or more embodiments, the amine reactive moiety can include N-hydroxysuccinimide or N-hydroxysulfosuccinimide.

In one or more embodiments, the thiol reactive moiety can include maleimide or iodoacetamide.

As used herein, the term "thiolated HA binding peptides" means the HABPep disclosed herein which has been chemically modified, using known means in the art, to covalently attach one or more thiol (SH) moieties to the peptide.

One of ordinary skill in the art will understand that the chemical modifications to the biopolymers to incorporate the amine reactive moieties and thiol reactive moieties are known in the art and can be accomplished using known methods.

In accordance with an embodiment, the present invention provides a method for coating a tissue surface with a biologically compatible polymer having one or more HA binding peptides comprising: a) contacting the tissue surface with an effective amount of the bifunctional biopolymer composition described herein for a time sufficient to create a thiol reactive tissue surface; and b) contacting the tissue surface of a) with an effective amount of thiolated HA binding peptides to create a tissue surface coated with a biologically compatible polymer having one or more HA binding peptides.

In accordance with an embodiment, the present invention provides a method of treating a cartilage defect in a tissue of a subject comprising: a) administering to the tissue of the subject in need of treatment, an effective amount of the bifunctional biopolymer composition described herein for a time sufficient to create a thiol reactive tissue surface on the cartilage defect; and b) administering to the tissue of the subject in need of treatment, an effective amount of thiolated HA binding peptides to create a cartilage defect coated with a biologically compatible polymer having one or more HA binding peptides.

In one or more embodiments, the at least one amine reactive moiety of the bifunctional biopolymer composition described herein is N-hydroxysuccinimide.

In one or more embodiments, the at least one thiol reactive moiety of the bifunctional biopolymer composition described herein is maleimide.

In one or more embodiments, the biologically compatible polymer of the bifunctional biopolymer composition described herein is PEG.

It will be understood that the bifunctional biopolymer compositions can include other suitable amine and thiol reactive moieties known in the art. Examples would include N-hydroxysulfosuccinimide and iodoacetamide.

In accordance with some embodiments, the bifunctional biopolymer composition is administered or applied prior to administration of the thiolated HA binding peptides. In other embodiments, the bifunctional biopolymer composition is administered or applied concurrently with the thiolated HA binding peptides.

EXAMPLES

Synthesis and Purification of HABPep: HA binding peptide (HABPep: GAHWQFNALTVR) (SEQ ID NO: 1) was synthesized by Fmoc-mediated solid phase peptide coupling methods from Wang resin (Novabiochem). High performance liquid chromatography (HPLC: C18 Vydac column) was used to purify the peptide. Product was lyophilized and stored at −20° C. The molecular weight of the product was confirmed by Matrix-assisted laser-desorption ionization time-of-flight mass spectrometry (MALDI-TOF MS, Voyager DE-STR, Applied Biosystems). HABPep: mass calcd: 1399.58 [M+H]+; mass found: 1399.40 [M+H]+

Synthesis and purification of acryloly-PEG-HABPep. Acryloyl (ACRL)-PEG-HABPep was prepared following the modified method of Hern and Hubbell. Twenty milligram of HABPep was dissolved in 10 mL of 50 mm sodium bicarbonate solution. ACRL-PEG-N-hydroxysuccinimide (ACRL-PEG-NHS) (Nektar, molecular weight: 3400, 70.9 mg, 20.9 µmol) was dissolved in 2 mL of 50 mm sodium bicarbonate solution and the resulting solution was added drop-wise to the HABPep solution. The solution was shaken on an orbital shaker for 2 hours at room temperature. Ultrafiltration (Millipore, molecular weight cut off=3500 Da) was used to remove unreacted HABPep and ACRL-PEG-NHS, and the solution containing the pure product was lyophilized. The dried powder was dissolved in deionized water and run through a Sephadex G-25 size exclusion column (Pharmacia) to remove small molecule impurities. Elution fractions containing the target product were combined and lyophilized. The molecular weight of the target product was confirmed by MALDI-TOF mass spectrometry. The product was stored at −20° C. and used within a week.

Photoencapsulation of HA. Macromer solution was prepared by mixing 5 mg/ml HA, 0.05% (w/v) photoreactive initiator (Igracune 2959; Ciba Speciality Chemicals), 2% (w/v) ACRL-PEG-HABpep and 8% (w/v) PEODA (SunBio, molecular weight: 3400 g/mol) in PBS. The solution was photopolymerized by UV exposure (EXFO Acticure 4000; wavelength: 365 nm; intensity: ~5 mW/cm$^2$) and formed a solid hydrogel constructs.

The hydrogel constructs were incubated in 1 ml PBS or hyaluronidase (50 Um') solutions. Solutions were collected at various time points and frozen at −20 degree Celsius till the carbazole assay.

Carbazole Assay. Sodium tetraborahydrate is made by dissolving 191 mg of sodium tetraborahydrate in 20 ml of sulfuric acid. A 0.125% (w/w) carbazole solution is made by dissolving 0.0125 grams of carbazole in 9.9875 grams of ethanol. Sodium tetraborahydrate (3 ml) were placed in test tubes and cooled to 4 degrees Celsius. The glucuronic acid standards (0.5 ml) were carefully layered over the sodium tetraborahydrate. The closed tubes were shaken gently at first and then vigorously with constant cooling. Tubes were then heated for 10 minutes in a boiling hot water bath and cooled to room temperature. Carbazole (0.1 ml) were then added to the tubes and shaken again. The test tubes were heated in a boiling water bath once more for 15 minutes and cooled down to room temperature. Absorption of the samples was measured at 530 nm against blanks (distilled water).

Chondrogenic differentiation of goat mesenchymal stem cells. Goat bone-marrow derived mesenchymal stem cells (MSCs) were isolated and expanded as previously described (19). After three or four passages, MSCs were trypsinized, centrifuged, and resuspended in a macromer solution containing 10% PEGDA and 2% acryl-PEG-peptide or PEGMA as well as varying HA concentrations (0, 0.5, 2.5, 5 mg/ml). Cells were suspended at 20 million/ml and hydrogels polymerized in 100 µl cylindrical molds as described above. Hydrogel constructs were transferred to 24-well plates containing chondrogenic differentiation medium containing 100 nM dexamethasone (Sigma), 40 mg/L Proline (Sigma), 50 mg/L ascorbic acid-2-phosphate (Sigma), 100 mg/L sodium pyruvate (Invitrogen), 50 mg/ml ITS Premix (insulin, transferring, selenous acid; BD Biosciences), 1% penicillin/streptomycin (Invitrogen), and 10 ng/ml transforming growth factor β (TGFβ-1). Constructs were cultured for up to 6 weeks, after which they were evaluated on the basis of biochemical content, chondrogenic gene expression, and histological analysis.

Biochemical characterization of in vitro chondrogenesis. Hydrogel constructs were harvested at time points up to 6 weeks for biochemical analysis as previously described (Tissue Engineering, 9:679-88 2003). Constructs were weighed, lyophilized, and weighed again to obtain a dry weight and swelling ratio. Dried hydrogels were homogenized with pellet pestles and digested overnight in papain (Worthington Biochemical). DNA content was assayed using Hoescht 33258 dye (Molecular Probes) and a DynaQuant fluorometer (Model and manufacturer) against a calf thymus DNA standard curve. Glycosaminoglycan (GAG) content was assayed by measuring absorbance at 525 nm with dimethylmethylene blue (DMMB) dye against a standard curve using chondrotin sulfate C (Sigma). A hydroxyproline assay was used to determine collagen content by hydrolysis overnight in hydrochloric acid followed by reaction with p-dimethylaminobenzaldehyde (Sigma) and chloramine T (Sigma). Absorbance was read on a spectrophotometer at 563 nm and compared to hydroxyproline standards (Sigma). Biochemical content was normalized to DNA content and dry weight to account for variations in construct size and cellularity. All biochemical data had a sample size of 4.

Histological characterization of in vitro chondrogenesis. Hydrogel constructs were fixed in 4% paraformaldehyde (Sigma) and stored in 70% ethanol. Constructs were dehydrated, embedded in paraffin, and sectioned into 5 nm sections using a microtome (Leica). Sections were stained with Safranin O to assess GAG content. Immunohistochemistry was performed using rabbit polyclonal antibodies against type I and type II collagen followed by visualization with horseradish peroxidase using the Histostain SP kit (Invitrogen). Images were captured using a Zeiss Axiovert microscope.

Real time polymerase chain reaction analysis of in vitro chondrogenesis. Constructs were homogenized with pellet pestles and RNA was isolated from three separate constructs using Trizol (Invitrogen) following standard protocols. RNA concentrations were obtained using a Nanodrop 2000 spectrophotometer. One µg of RNA was reverse-transcribed to cDNA using the Superscript First Strand Synthesis kit (Invitrogen). Real-time polymerase chain reaction (PCR) was performed on the cDNA using a Step One Plus system (Applied Biosystems) and SYBR Green master mix (Applied Biosystems) using primers shown in Table 1. Relative expression levels compared to β-actin were determined using the $2^{-\Delta\Delta Ct}$ method. The reference condition chosen was PEGMA scaffolds containing no encapsulated HA at 4 days; all data was normalized to this condition.

TABLE 1

Primer sequences for RT-PCR

| Target | | Sequence |
|---|---|---|
| B-actin | Forward | 5'-GGCACCCAGCACAATGAA-3' (SEQ ID NO: 6) |
| | Reverse | 5'-GCTAACAGTCCGCCTAGAAGC-3' (SEQ ID NO: 7) |
| Aggrecan | Forward | 5'-CACGATGCCTTTCACCACGAC-3' (SEQ ID NO: 8) |
| | Reverse | 5'-TGCGGGTCAACAGTGCCTATC-3' (SEQ ID NO: 9) |
| Type I collagen | Forward | 5'-AGGGCCAAGACGAAGACATC-3' (SEQ ID NO: 10) |
| | Reverse | 5'-AGATCACGTCATCGCACAACA-3' (SEQ ID NO: 11) |
| Type II collagen | Forward | 5'-GTGGAGCAGCAAGAGCAAGGA-3' (SEQ ID NO: 12) |
| | Reverse | 5'-CTTGCCCCACTTACCAGTGTG-3' (SEQ ID NO: 13) |
| Sox-9 | Forward | 5'-CGAGGAGGCCCCGGAACAGA-3' (SEQ ID NO: 14) |
| | Reverse | 5'-GCACCTCGCTCATGCCGGAG-3' (SEQ ID NO: 15) |

In vivo osteochondral defect model. A rat osteochondral defect model was used to assess the potential of HA binding hydrogels to effect in vivo repair. All animal procedures were approved by the Johns Hopkins Animal Care and Use Committee (protocol #RA08A450). Male Sprague-Dawley rats (8 weeks) were anesthetized with 2-3% Isoflurane using a tabletop anesthesia system (VetEquip). Hind limbs prepared using standard aseptic techniques, and an incision was made medial to the patellar tendon. The patella was displaced laterally to expose the articular surface of the femur. Round, 1 mm osteochondral defects were made in the patellar groove of the femur approximately 3 mm anterior to the ACL insertion point up to a depth of 1 mm. Defect depth was designed to approximate the depth used for microfracture procedures. Cartilage defect size was standardized through the use of a constant diameter drill bit to control defect diameter at 1 mm. Defect depth was controlled by drilling to a previously marked point on the bit.

Following defect creation, macromer solutions containing 10% PEGDA, 2% acryl-PEG-HABPep (or sHABPep), and 0.05% photoinitiator in PBS were placed into the defect site. Polymer solutions were photopolymerized by exposure to ultraviolet light for 5 minutes (365 nm, 5 mW/cm2, Acticure 4000). During polymerization, hydrogels were partially mixed with blood and bone marrow that was present during the defect creation. Controls included scrambled peptide hydrogels and untreated defects. Incisions were closed and animals were allowed unrestricted movement for the duration of the study. A sample size of 6 knees was used for each material condition at each time point (4 days, 3 weeks, 6 weeks).

Histological evaluation of in vivo repair. At each time point, knees were dissected and excised. Implant areas were grossly imaged using a Zeiss Axiovert dissection microscope. Knees were decalcified and fixed for approximately a week in a solution of 10% formalin and 10% formic acid. Solution changes were performed every other day, at which point solutions were qualitatively assayed for calcium content using an oxalate precipitation test. Following a negative test, samples were immersed in increasing concentrations of a sucrose solution (up to 20% w/v) as a cryoprotectant, taking care to give adequate time for full tissue penetration. Then, samples were immersed in graded solutions of 20% sucrose and OCT solution (Tissue-Tek), embedded in OCT, and frozen. Knees were cryosectioned at −20° C. using a cryostat microtome (Leica) to section thicknesses of 7-10 µm. Sections were stained with Safranin-O and Masson's Trichrome to visualize tissue morphology and repair.

Photoencapsulation of MSCs in hydrogel. MSCs were isolated from bone marrow as previously described (Tissue Eng., 2003; 9:679-688) and expanded in mesenchymal stem cell growth medium (Cambrex Bioscience). Macromer solution was prepared as described previously. Harvested MSCs were resuspended in the macromer solution (100 µL) at a concentration of 20×10$^6$ cells per mL, and the solution was photopolymerized by UV as described earlier. The hydrogel construct was cultured in chondrogenic medium with 10 ng/mL TGFβ-1 (RDI) for three weeks.

In vivo experiments. Athymic, nude mice were anesthetized with methoxyflurane. The hydrogel constructs of the present invention, after three-week in vitro culture, were placed subcutaneously. The animals were allowed to recover and move freely for 6 weeks until they were euthanized. The animal protocol was approved by the Hopkins Animal Care and Use Committee.

Biochemical Analysis and immunostaining. The hydrogel constructs (n=3) were lyophilized and papain digested. DNA content was determined with 33258 Hoechst dye. Glycosaminoglycan (GAG) content was determined by DMMB dye, and total collagen content, by hydroxyproline assay. Hydrogels were fixed overnight in 4% paraformaldehyde and prepared using standard histology techniques. Sections of a construct were stained for Safranin-O.

Data and data analysis. All experiments were performed in triplicate. The $OD_{530}$ data were averaged and standard deviation calculated using Excel (Microsoft, Redmond, Wash.). Hydrogel with 0 mg/ml HA did not yield any detection of uronic acid by Carbazole assay (data not shown). Quantitative biochemical data was evaluated using multifactor analysis of variance (ANOVA) to determine the significance of main factor effects to a significance level of 0.05. Multiple comparisons of individual condition means was carried out using Tukey's honestly significant difference (HSD) test. Statistical analysis was carried out in MATLAB (Mathworks).

Synthesis of hyaluronic acid binding peptide for lubrication/coating experiments. Thiolated hyaluronic acid binding peptide (C-HABPep; sequence CRRDDGAHWQFNALTVR) (SEQ ID NO: 2) was synthesized using standard Fmoc-mediated solid phase peptide synthesis on a Symphony Quartet peptide synthesizer (Protein Technologies). Following synthesis, peptides were cleaved using a solution of trifluoroacetic acid, triisopropylsilane, and water in a 95:2.5:2.5 ratio. Crude product was purified using reverse-phase high performance liquid chromatography (HPLC, C18 Grace-Vydac column) on a water/acetonitrile gradient. Purified peptides were frozen and lyophilized; identity of purified peptides was confirmed using matrix assisted laser-desorption ionization time of flight (MALDI-TOF) mass spectroscopy (Voyager DE-STR, Applied Biosystems).

Preparation of HA-binding coatings for lubrication/coating experiments. C-HABPep was conjugated to articular cartilage through a heterobifunctional poly(ethylene glycol) (PEG) spacer. Maleimide-PEG-N-hydroxysuccinimide (MAL-PEG-NHS, 3.4 kDa, Jenkem Technologies), which has functionalities that are thiol- and amine-reactive, was dissolved to 5 mM in 50 mM sodium bicarbonate, pH 7.5 and added to the articular surface. The NHS groups were allowed to react with endogenous amines on the cartilage surface for 30 minutes. PEGylation was confirmed by attenuated total reflectance Fourier transform IR spectroscopy (ATR-FTIR; Bruker Vector 22 with a Pike Miracle ATR attachment). Following thorough washes in buffer to remove unreacted crosslinker, a 1.5 mM solution of C-HABPep was added to the surface to react with maleimide groups for an additional 30 minutes. Surfaces were carefully washed to remove unreacted peptide, yielding a cartilage surface with covalently attached HA-binding functionality.

X-ray photoelectron spectroscopy. XPS was performed to verify the presence of the HA-binding coating on articular cartilage. Lyophilized cartilage samples were adhered to the specimen stage and loaded into a PHI 5400 XPS instrument at ultra-high vacuum. The samples were analyzed using Mg Kα X-rays (1253.6 eV), and spectra were acquired at a take-off angle of 45°. Atomic concentrations were determined by integration of the relevant photoelectron peaks using commercially available software (CasaXPS).

Visualization of the HA-bound layer. Cartilage was conjugated with C-HABPep and incubated with biotinylated HA synthesized as previously described. Briefly, HA (975 kDa) was dissolved in 50 mM boric acid, pH 5.2 at 2 mg/ml. This was combined with biotin hydrazide (Sigma) in a 20:1 weight ratio. N-(3-Dimethylaminopropyl)-N'-ethylcarbodiimide hydrochloride (EDC, Sigma) was added to a final concentration of 100 mM. The reaction was allowed to proceed at room temperature for 16 hours, after which it was dialyzed to remove unreacted biotin hydrazide and EDC. HA-biotin was lyophilized and stored at −20° C. for later use. Following incubation with 5 mg/ml HA-biotin, HAB-Pep-functionalized cartilage samples were washed vigorously to remove unbound HA-biotin. Presence of biotin was visualized using streptavidin and horseradish peroxidase based on the Histostain SP kit (Invitrogen).

Cartilage sample preparation for lubrication testing. Cartilage samples were prepared for lubrication testing as a modification on previously published protocols (Arthritis and Rheumatism 56, 882-891, (2007); Osteoarthritis Cartilage 15, 35-47, (2007)). Briefly, adult bovine femurs were isolated and the patellar groove was exposed. Care was taken to avoid damaging the articular surface during dissection. Biopsy punches were used to isolate cylindrical disks (radius=6 mm) and annuli (outer radius=4 mm, inner radius=1.5 mm) with small holes punctured through the cylinder walls to improve fluid depressurization. Cartilage was used fresh without freezing or the addition of protease inhibitors so as not to change the surface lubrication properties. Samples were shaken in phosphate buffered saline (PBS, Invitrogen) overnight to deplete the cartilage surface of any residual synovial fluid, after which they were functionalized with an HA-binding layer as needed and incubated at 4° C. for ~24 hours in the test lubricant. Following incubation in the lubricant, boundary lubrication testing was performed.

Lubrication testing. Boundary lubrication testing of articular cartilage-cartilage contacts was performed by modifying a previously published protocol (Arthritis and rheumatism 56, 882-891 2007; Osteoarthritis Cartilage 15, 35-47, 2006). Briefly, a cartilage disk and annulus were adhered with cyanoacrylate glue to parallel plate fixtures of a RFS-3 rheometer (Rheometric Scientific). The samples were bathed in the test lubricant, measured with digital calipers, compressed to 82% of their original combined height, and preconditioned by rotating 2 revolutions in each direction at an effective sliding velocity of 3 mm/s, which is defined as the angular velocity times the effective radius of the annulus Reff=⅔[$(R_o^3-R_i^3)/(R_o^2-R_i^2)$]=2.94 mm. This preconditioning was repeated twice more, followed by a two hour stress-relaxation period to allow the pressurization of the fluid in the compressed cartilage to fully subside, leaving only boundary effects for the lubrication testing.

Lubrication testing was then performed by 2 rotations in each direction at an effective sliding velocity of 0.3 mm/s Samples were allowed to relax between tests for 1200, 120, 12, and 1.2 seconds. Lubrication testing was then carried out by reversing the order of the revolutions (turning first clockwise instead of counter-clockwise) with the same pre-test relaxation periods as before. During each test, torque (t) and normal force (N) were measured, and instantaneous measurements of $\mu_k$, the kinetic friction coefficient, where determined from the following equation: $\mu_k=\tau/(R_{eff}*N)$. Instantaneous $\mu_k$ values were averaged over the second revolution in each direction to produce an average $<\mu_k>$ that was used for comparisons. Generally, differences between coefficients for forward and backward revolutions were very small, so $<\mu_k>$ data shown is only from a single direction of rotation. Static friction coefficients were calculated as the instantaneous $\mu_s=\tau_{max}/(R_{eff}*N)$ at the maximal torque value found during the startup period of the test.

Example 1

Figure 3:
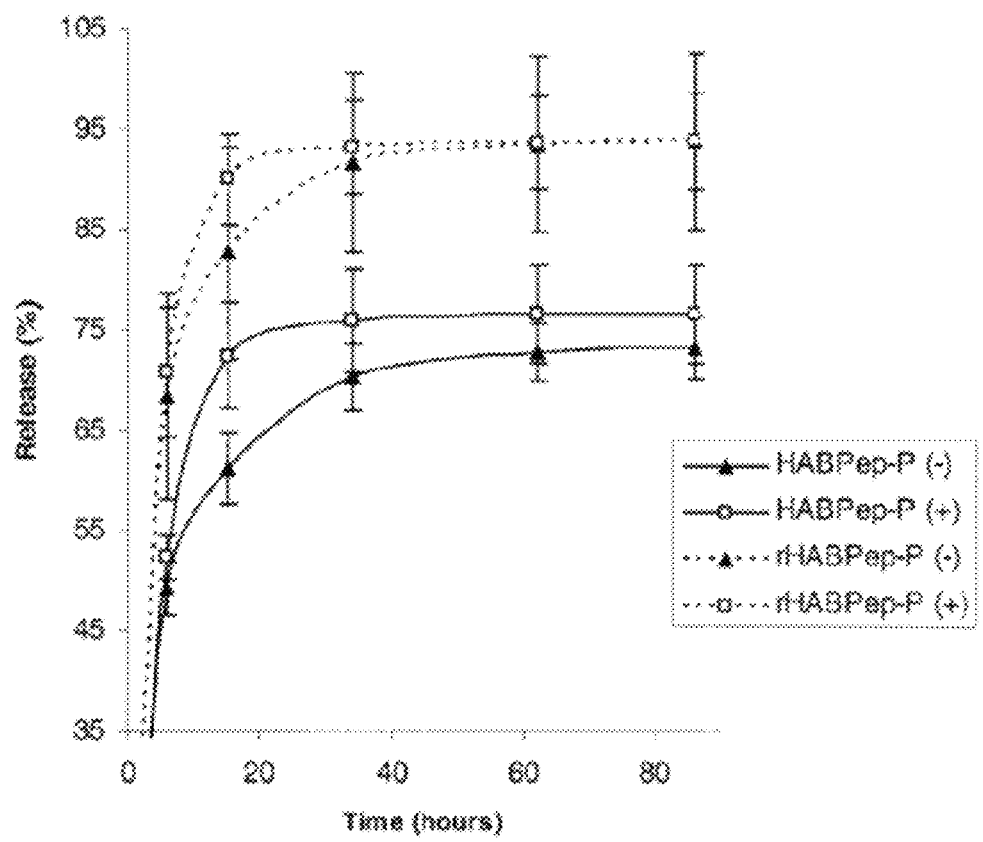
FIG. 3 depicts Degradation profiles of 5 mg/ml HA from 10% PEODA without (−) or with (+) 50 Um' hyaluronidase. HA-encapsulated PEODA (100 µL) were incubated in 1 ml PBS or hyaluronase solution with or without 2% HA-binding peptide at 37° C. while placed on a shaker. (HAB-Pep-P: HA-binding peptide, rHABPep-P: randomly sequenced peptide with the same composition as the HA-binding peptides.) Solutions were replaced and collected at various time points, and carbazole assay was employed to measure the release of HA degradation to PBS solution by detecting uronic acid.

HA-encapsulated PEODA hydrogels of the present invention (100 μL) were incubated in 1 ml PBS or hyaluronase solution with or without 2% HA-binding peptide at 37° C. while placed on a shaker. (HABPep-P: HA-binding peptide, rHABPep-P: randomly sequenced peptide with the same composition as the HA-binding peptides). Solutions were replaced and collected at various time points, and carbazole assay was employed to measure the release of HA degradation to PBS solution by detecting uronic acid. (FIG. 3).

Example 2

Figure 4:
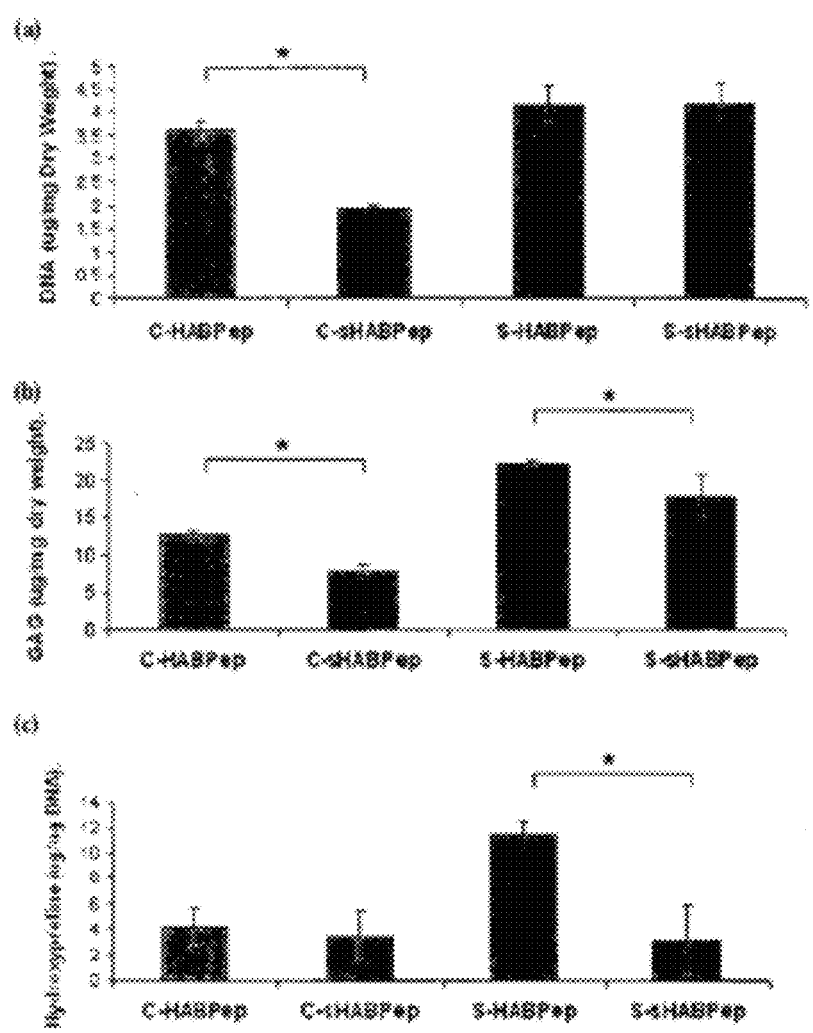
FIG. 4 depicts Retention of HA by crosslinking HABPep results in increased DNA and GAG in constructs after three-week in vitro culture. Moreover, simple addition of soluble HABPep in a construct increases GAG and collagen contents. (C-HABPep: crosslinked HABPeptide, C-sHAB-Pep: crosslinked randomly sequenced HABPeptide, S-HABPep: soluble HABPeptide, S-sHABPep: soluble randomly sequenced HABPep).

FIG. 4 shows the retention of HA by crosslinking HAB-Pep results in increased DNA and GAG in hydrogel constructs after three-week in vitro culture. Moreover, simple addition of soluble HABPeptide in a construct increases GAG and collagen contents. (C-HABPep: crosslinked HAB-Peptide, C-sHABPep: crosslinked randomly sequenced HABPeptide, S-HABPep: soluble HABPeptide, S-sHAB-Pep: soluble randomly sequenced HABPep).

Example 3

Figure 5:
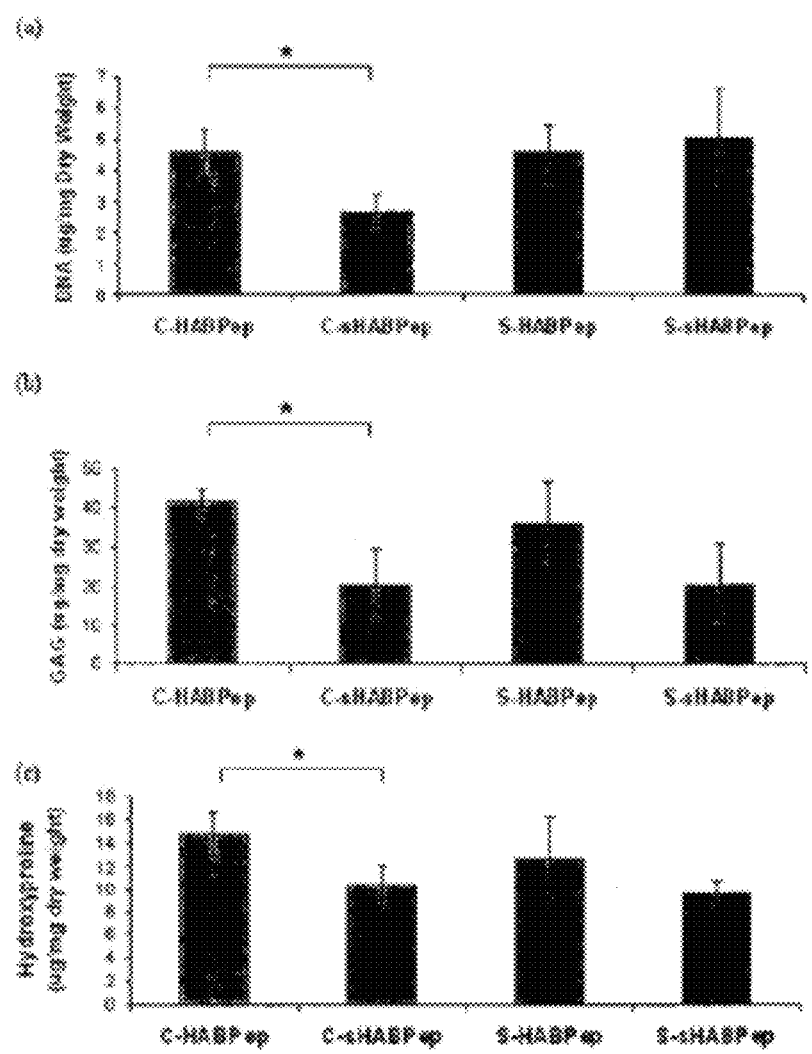
FIG. 5 depicts that after three-weeks of in vivo culture, retention of HA by crosslinking HABpep (CHABPep: crosslinked HABP) still results in increased DNA and GAG in constructs.

FIG. 5 shows that after three-weeks of in vivo culture, retention of HA by crosslinking HABpep (CHABPep: crosslinked HABP) still results in increased DNA and GAG in constructs.

Example 4

Figure 6:
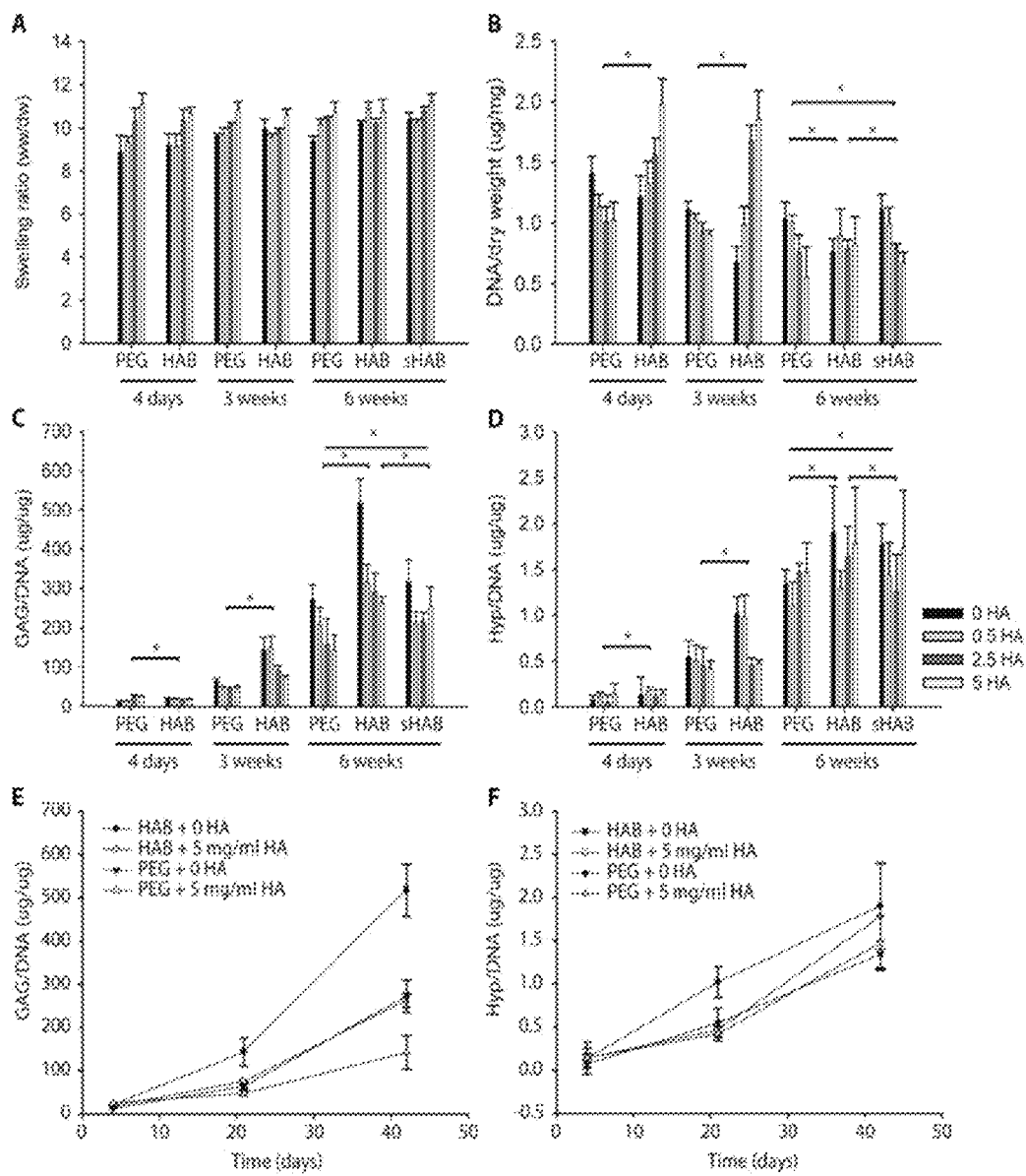
FIG. 6 depicts HA-interacting hydrogels increased cartilage production by MSCs. (6A) Physical properties of PEG, HA-interacting (HAB), and scrambled peptide control (sHAB) hydrogels containing encapsulated MSCs varied with initial HA loading and culture time. Swelling was significantly dependent on HA loading (p<0.05). (6B) Cell number, as measured by DNA content, was initially highly dependent on scaffold type and HA loading, but differences decreased as scaffolds matured at 6 weeks. DNA was significantly dependent on hydrogel type and time but not HA loading (p<0.05). (6C) Glycosaminoglycan (GAG) content, normalized to DNA, increased with time for all scaffolds, with strong HA dose dependence at later weeks. GAG levels were significantly dependent on hydrogel type, HA loading, and time (p<0.05). (6D) Overall collagen production, as measured by hydroxyproline content normalized to DNA, increased over time for all scaffolds but showed no specific trend across HA concentrations. Collagen content was significantly dependent on hydrogel type and time but not HA loading (p<0.05). GAG content (6E) and collagen content (6F) were plotted for representative HAB and PEG conditions over time.

Chondrogenic differentiation of MSCs in HA-binding PEG hydrogels. Cartilage formation by MSCs improved in HA-interacting scaffolds as evaluated by biochemical content, gene expression, and histological analysis. MSCs were encapsulated in HA-interacting scaffolds containing varying concentrations of HA and incubated in chondrogenic medium for 6 weeks. The physical properties of these hydrogels varied depending on initial HA content and changed over the course of chondrogenic differentiation (FIG. 6A). At 4 days, the swelling ratio of HA-interacting and control hydrogels increased in an HA dose-dependent manner. However, as tissue developed over the culture period, the water content in the hydrogels varied. Swelling ratio depended significantly ($p<0.05$) as a function of HA loading, and showed significant interactions between HA loading and time as well as hydrogel choice and time. Swelling did not directly depend on time or hydrogel choice (data not shown).

HA-binding hydrogels increased cartilage production as determined by extracellular matrix production, cell number, and gene expression analysis. DNA content, or cell number, in the control PEG hydrogels decreased in an HA dose-dependent manner at all time points, but increased in HA-binding hydrogels containing increasing levels of exogenous HA at 4 days and 3 weeks. However, at later time points (6 weeks), DNA levels in the HA-interacting hydrogels decreased (FIG. 6B). Overall, DNA content depended significantly ($p<0.05$) as a function of time and hydrogel choice. While HA loading was not a significant main effect, it demonstrated significant interactions with both time and hydrogel choice (data not shown). Glycosaminoglycan (GAG) deposition in the hydrogels increased over time in all conditions (FIG. 6C. E). However, GAG levels decreased with higher exogenous HA loading in a dose-dependent manner for both control and HA-interacting hydrogels. HA-binding hydrogels produced significantly greater GAG levels than PEG and sHABPep controls, and hydrogels without any exogenous HA produced the greatest GAG matrix levels compared to all groups. GAG content depended significantly on all main factor effects ($p<0.05$) and HA loading demonstrated significant interactions with both time and hydrogel choice (data not shown). Total collagen deposition, represented by hydroxyproline content, in both HA-interacting and control hydrogels also increased over 6 weeks of chondrogenic culture (FIG. 6D, F). Hydroxyproline content depended significantly on hydrogel choice and time ($p<0.05$), and HA loading interacted significantly with time (data not shown). Overall, the extracellular matrix analysis in the hydrogels suggests that the HA-interacting hydrogels with little to no exogenous HA loading produced the greatest levels of new cartilage production.

Example 5

Figure 7:
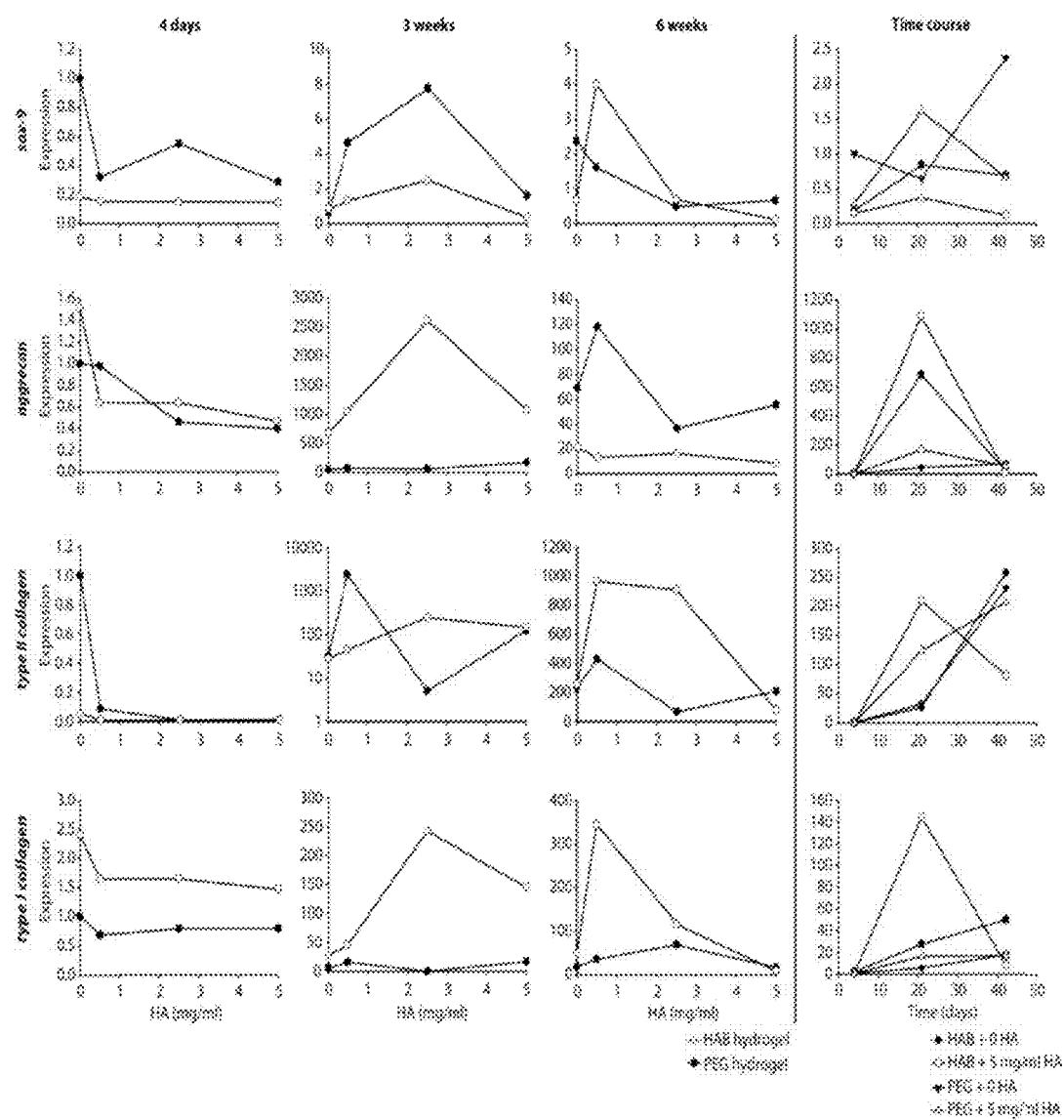
FIG. 7 depicts gene expression demonstrates chondrogenic differentiation of MSCs in HA-interacting hydrogels. Sox-9, aggrecan, type II collagen, and type I collagen expression were analyzed for all hydrogel conditions. All expression levels were normalized to individual β-actin levels and observed expression for PEG scaffolds containing no HA at 4 days. HA-interacting hydrogels increased aggrecan production at 3 weeks and type II collagen production at 6 weeks.

Gene expression analysis of cartilage-related markers supported the chondrogenic differentiation of MSCs in the hydrogels (FIG. 7). Expression of aggrecan, an important protein in GAG structure and assembly, was largely unchanged at 4 days between HA-interacting and control hydrogels, though decreased with increasing HA loading. At 3 weeks, HA-interacting hydrogels demonstrated dramatically higher aggrecan expression than control hydrogels, peaking at 2.5 mg/ml exogenous HA loading. However at 6 weeks, the control hydrogels expressed higher levels of aggrecan compared to HA-binding hydrogels, with exogenous HA producing a dose-dependent decrease in expression. In the case of type II collagen, no significant differences were observed between HA binding hydrogels and controls at 4 days and 3 weeks, while intermediate HA loading of HA-binding hydrogels exhibited a significant upregulation at 6 weeks. Levels of type I collagen expression were also upregulated in HA-binding hydrogels, but to a much lesser degree than the upregulation of type II collagen and aggrecan.

Example 6

Figure 8:
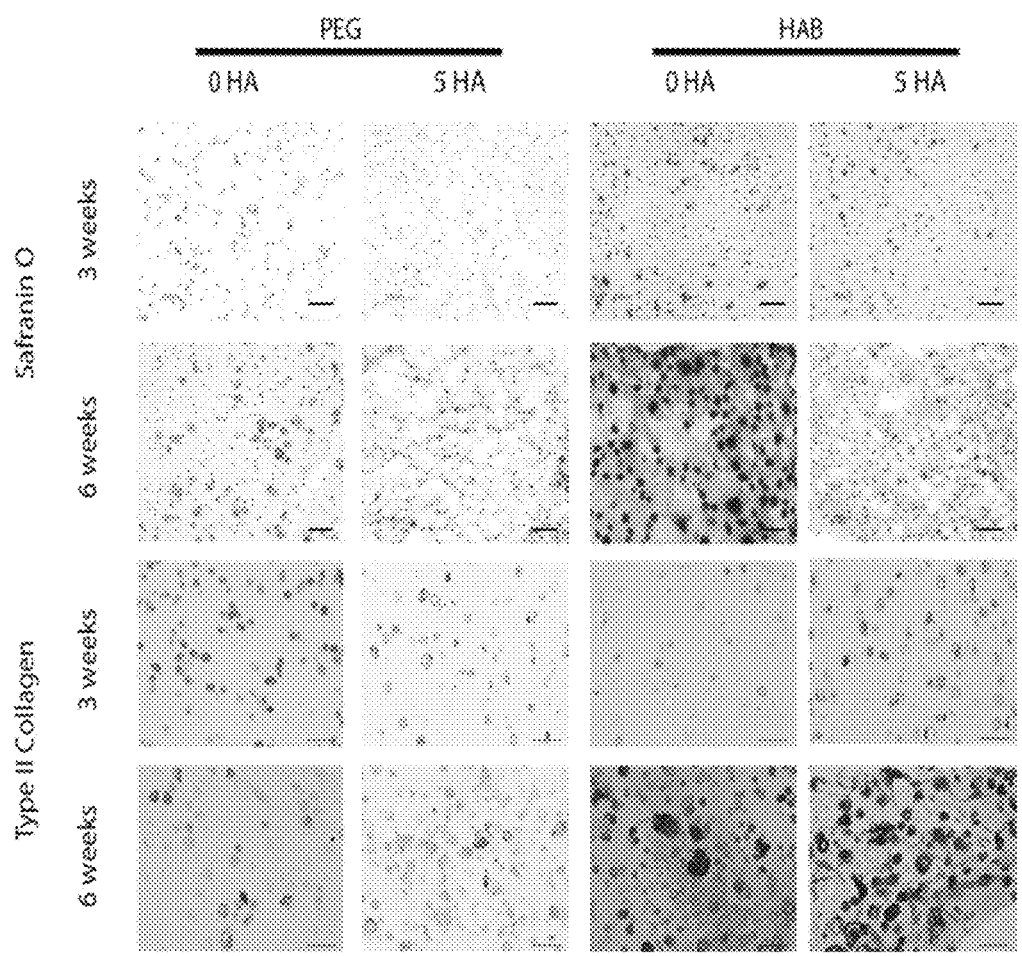
FIG. 8 depicts HA-interactive scaffolds accumulate more cartilage matrix components at 6 weeks. Safranin O staining of HA-interactive scaffolds and PEG scaffolds across 6 weeks demonstrate increased GAG deposition in HA-interactive scaffolds. Staining is highest for low HA loadings Immunohistochemical staining for Type II collagen indicated initially higher staining for PEG controls at 3 weeks, but substantially higher staining for HA-interactive scaffolds at 6 weeks. Bar=100 µm.

Histological analysis supports the biochemical results that the HA-interactive scaffolds produce greater levels of cartilage tissue components after 6 weeks. Safranin O staining of harvested constructs (FIG. 8) exhibited a substantial increase in GAG deposition in HA-interacting hydrogels at 3 weeks compared to controls. In addition to the concentrated GAG staining in the pericellular region, HA-binding hydrogels contained higher staining in the intercellular regions of the hydrogel material, suggesting the scaffold has retained cell-secreted proteoglycans by binding to the HA core. The differences in staining were less pronounced at 6 weeks between the groups, though HA-interactive scaffolds still had more intense staining. Safranin O staining was also a function of initial HA loading, with more intense staining observed for lower loading for both control and HA-binding scaffolds, similar to the quantified extracellular matrix results. Type II collagen immunostaining of control hydrogels at 3 weeks was slightly more intense than HA-interactive scaffolds. However, after 6 weeks, HA-binding PEG hydrogels produced significantly greater Type II collagen staining compared to PEG controls (data not shown).

Example 7

Repair of osteochondral defects in vivo with hydrogels. Implantation of HA-interactive PEG hydrogels increased cartilage tissue production in osteochondral defects created on the rat femoral condyle compared to control hydrogels and untreated defects. Acellular scaffolds were implanted in the defects to avoid the challenge of delivering exogenous cells. The implanted scaffolds were able to integrate with the surrounding tissue and gross images of harvested knees after 4 days following implantation demonstrated that hydrogels remained in the defects and achieved good material-tissue integration (FIG. 9).

Figure 9:
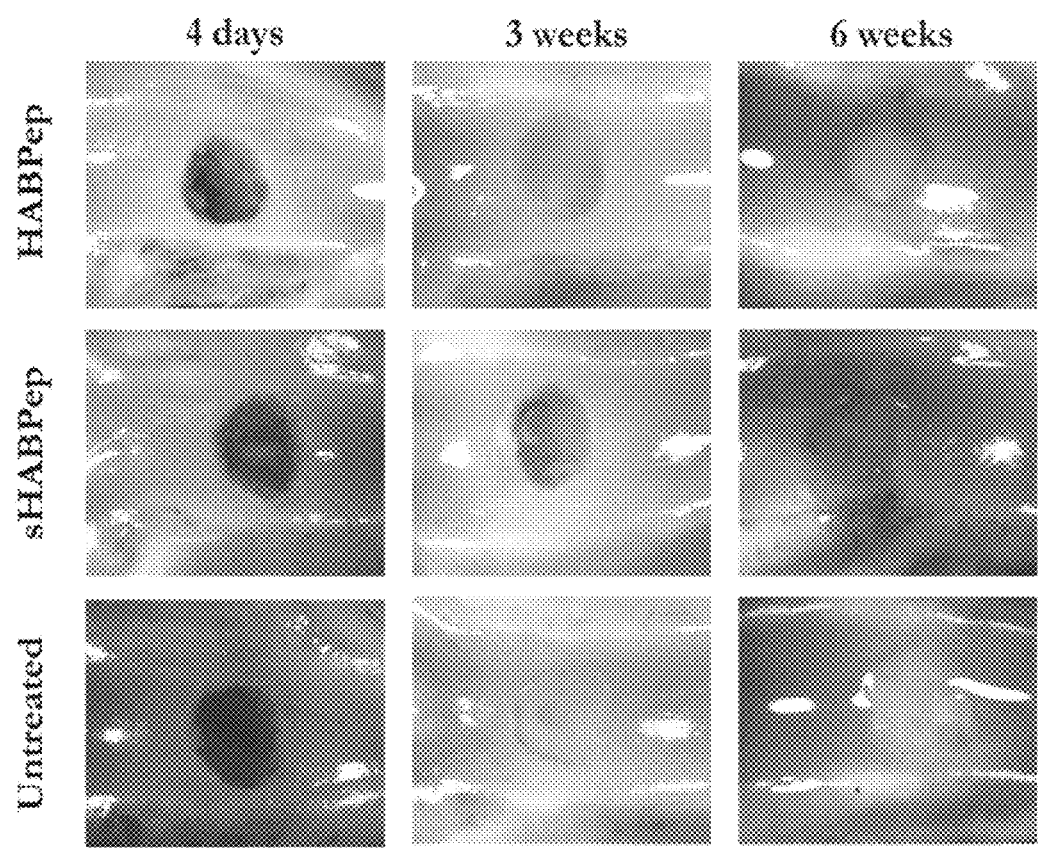
FIG. 9 shows gross images of representative cartilage defect repair. Cartilage defect repair over 6 weeks in vivo resulted in a repair tissue that varied between HA-interactive hydrogels (HABPep), scrambled peptide control hydrogels (sHABPep), and untreated defects.
Figure 10:
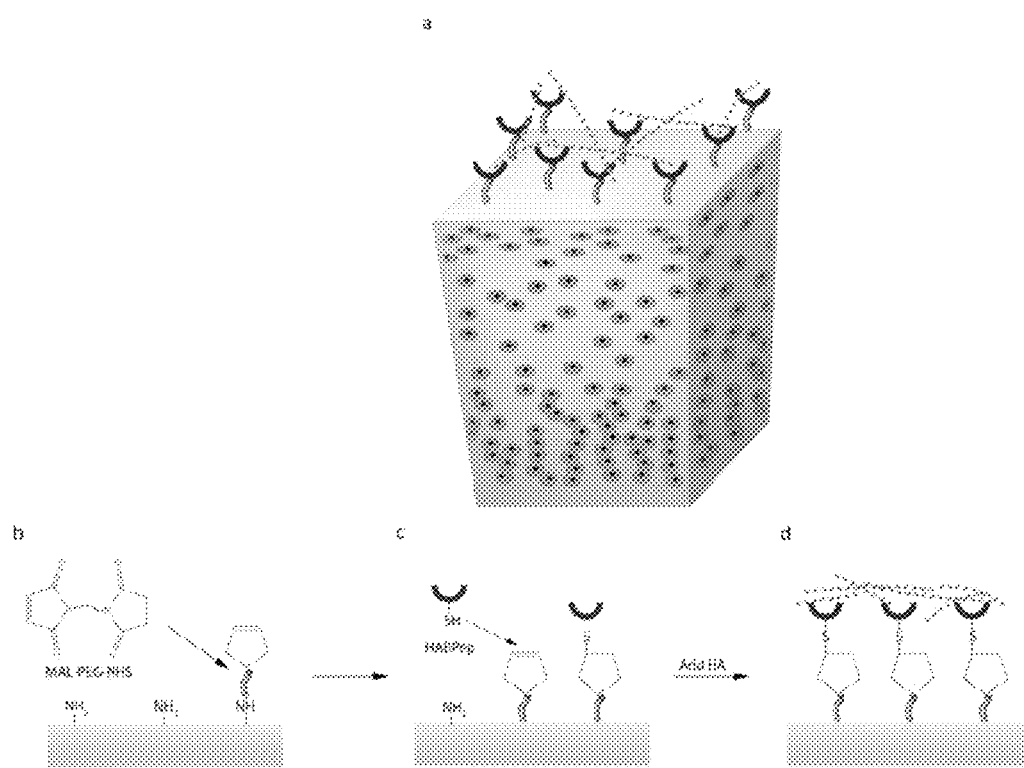
FIG. 10 depicts cartilage tissue surface modification with an HA binding polymer system. 10a, Schematic of cartilage surface modified with an HA-binding peptide designed to interact with and bind HA in surrounding fluid. 10b, The first step in the chemical procedure is reaction of a maleimide-PEG-NHS crosslinker with primary amines on the cartilage surface which creates an exposed thiol-reactive surface. 10c, A thiolated HA-binding peptide is then reacted to the maleimide. 10d, After exposure to an HA solution, the HA binds to the peptide-polymer coating on the cartilage surface.

Implantation of HA-interactive hydrogels in osteochondral defects resulted in a more robust cartilage tissue repair compared to control hydrogels and untreated defects (FIG. 9). After 4 days, discrete hydrogel material was clearly visible in the HA-interactive and scrambled-peptide control conditions, while the untreated defects were filled with a clot, cells, and tissue debris. Both HA-binding and control hydrogels appeared to be well-integrated into the surrounding tissue with cell infiltration present at the margins of the implants. Scrambled peptide controls exhibited a significantly stronger tissue response with more cells at the implant edge. After 3 weeks, implant material was still evident for both HA binding and control hydrogels, though the surrounding tissue response had mostly subsided and the underlying subchondral bone was undergoing repair. Although there was as yet no clear, differentiated cartilage-like repair tissue visible, there were some early signs of repair at the margins of the defect that did not stain positive for Safranin O. Untreated defect controls exhibited a smaller defect depth, but no visible Safranin O positive cartilage repair. At 6 weeks, implant material was entirely absent and replaced with varying levels of repair tissue. Neither HA-binding nor scrambled peptide control hydrogels caused a complete regeneration of healthy cartilage at this time point, but HA binding hydrogels produced a greater volume of repair tissue with stronger Safranin O staining compared to controls, though still weaker than healthy tissue. Untreated defects showed a well integrated repair tissue with minimal Safranin O staining, indicative of the expected fibrocartilagenous repair.

The presence of the HA-interactive hydrogels in the osteochondral defects also had an impact on the ECM of the cartilage surrounding the defect. At 3 weeks, all knees exhibited reduced Safranin O staining for GAGs on articular cartilage surrounding the defect and in the joint space compared to day 4 staining and untreated controls. At 6 weeks, Safranin O staining of cartilage outside the defect area was further reduced, suggesting the presence of a discrete osteochondral defect also caused degenerative joint changes. However, joints containing defects treated with HA-interactive scaffolds exhibited greater proteoglycan staining, indicating reduced cartilage degeneration. Overall, these results indicate that HA-binding hydrogels produced an improvement in the repair of osteochondral defects and the maintenance of cartilage tissue surrounding the defect.

Example 8

Figure 11:
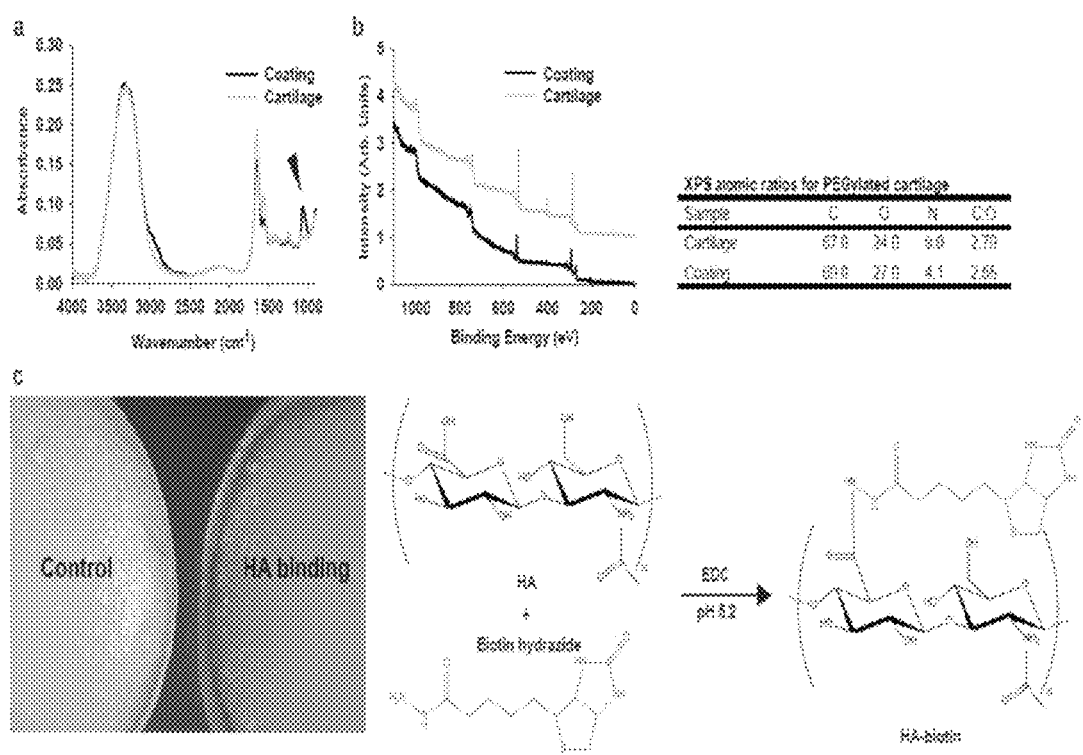
FIG. 11 shows the characterization of HA-binding polymer coating. 11a, PEG crosslinker reaction to articular cartilage was confirmed by ATR-FTIR that validated the presence of the ether-rich PEG coating with a large ether peak at ~1066 cm-1. 11b, PEGylation was further verified by XPS atomic ratios. Compared to unmodified cartilage, coated samples had a carbon to oxygen ratio closer to 2, the ratio in PEG, and significantly lower nitrogen content. 11c, HA-binding functionality of the peptide-conjugated cartilage was visualized using a biotinylated HA. Biotinylated HA was synthesized and applied to cartilage modified with the HA-binding polymer system and native, unmodified cartilage. After thorough washing, the biotinylated HA was treated with strepavidin and horseradish peroxidase to visualize. The tissue surfaces treated with the HA-binding polymer coating stained darker than the untreated native cartilage.

Articular cartilage tissue explants were functionalized with PEG spacers and HA-binding peptide (HABPep). The PEG spacer was functionalized with an amine-reactive N-hydroxysuccinimide (NHS) group as well as a thiol-reactive maleimide (MAL) group to generate the heterobifunctional NHS-PEG-MAL. The NHS-PEG-MAL was then reacted with the amine-rich cartilage surface to produce a thiol-reactive surface that could be readily exposed to a thiolated HABPep. PEGylation of articular cartilage was confirmed by attenuated total reflectance Fourier transform infrared (ATR-FTIR) spectroscopy that compared coated cartilage surfaces to unmodified control cartilage explants. Polymer-modified surfaces produced spectra that indicated a large peak at ~1066 cm$^{-1}$, consistent with the ether bonds of the PEG spacer, that was not present on unmodified cartilage, (FIG. 11A). Additionally, X-ray photoelectron spectroscopy (XPS) spectra of the PEGylated cartilage compared to native cartilage demonstrated a significant decrease in nitrogen content and a drop in the carbon to oxygen ratio (closer to 2, the ratio in PEG), indicating that a synthetic, lower-nitrogen containing layer had been successfully grafted to the cartilage surface (FIG. 11B). Thiolated HABPep was then readily grafted to the PEG-MAL coating. HA binding peptide functionalization of the polymer coating was confirmed by incubation of the cartilage with HA labeled using biotin hydrazide and 1-ethyl-3-(3-dimethylaminopropyl) carbodiimide. Following extensive washing, cartilage surfaces were incubated with streptavidin-conjugated horseradish peroxidase and stained to confirm the presence of HA-biotin. A greater intensity of staining was observed on material modified surfaces compared to control cartilage incubated with HA-biotin alone (FIG. 11C).

Example 9

Figure 12:
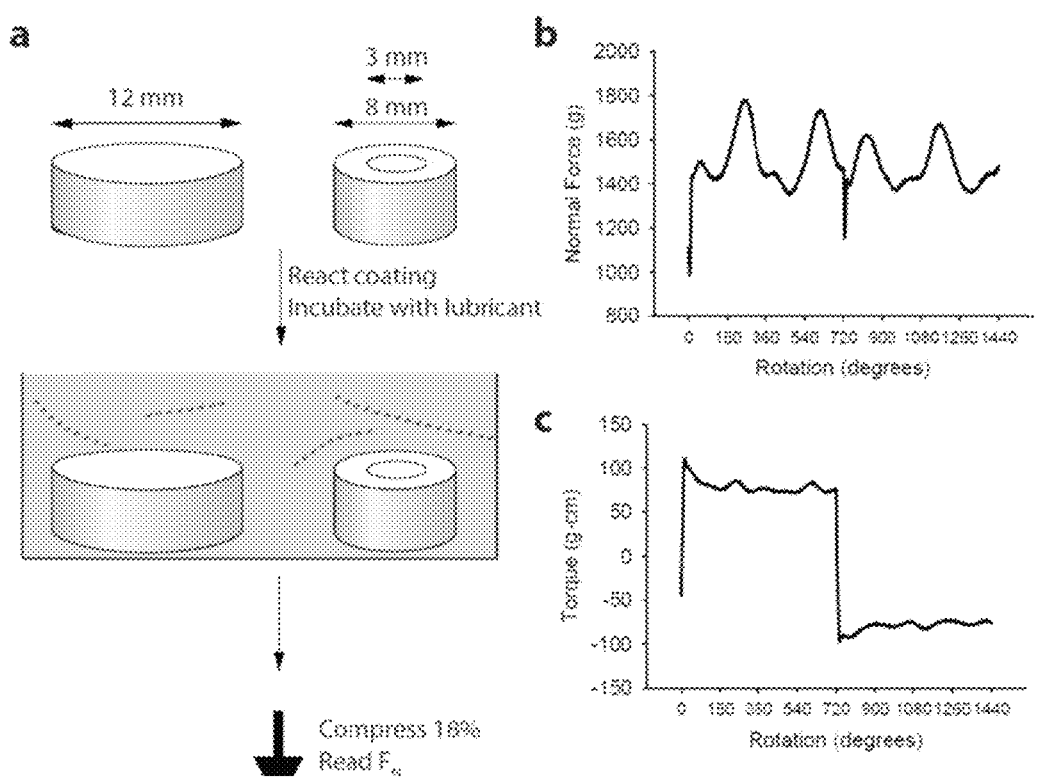
FIG. 12 depicts the boundary lubrication testing of articular cartilage. 12a, Boundary lubrication of articular cartilage was evaluated using a cartilage disk and annulus rotated in opposition. Cartilage samples were isolated and incubated in HA lubricant solutions or control PBS. Samples were compressed 18% and rotated 720° in each direction. Representative graphs of the 12b, normal force FN 12c, torque τ 12d, and instantaneous kinetic friction coefficient µkinetic are pictured for a control cartilage sample. Friction coefficients of the last 360° in each direction of rotation were averaged to determine an average $<\mu_{kinetic}>$, and the initial peak friction coefficient was determined to be $\mu_{static}$.

Boundary lubrication of native and polymer-modified cartilage surfaces was assessed using a modification of a rotational test protocol developed by Schmidt and Sah (FIG. 12A). Specifically, 8 mm cartilage annuli were compressed against 12 mm cartilage disks to 82% of original height, and rotated against each other at a physiologically relevant sliding velocity. The constant contact area and complete opposition of the cartilage samples eliminated lubrication effects arising from fluid pressurization, effectively isolating boundary lubrication effects for analysis. Coefficients of friction were derived from torque and normal force data. An example profile from a single test of native control cartilage is pictured in FIG. 3. Axial forces (FIG. 12B) exhibited periodic behavior of roughly the same period as the rotation. Measured torques (FIG. 12C) rose to a brief peak, and then stabilized in each direction of rotation. Calculated kinetic friction coefficients (FIG. 12D) were relatively stable by the second rotation in each direction after start-up behavior had subsided. Static friction coefficients were estimated from the start-up peak in the instantaneous kinetic friction.

Example 10

Cartilage explants were bathed in HA solutions to evaluate boundary lubrication. Two concentrations of ~1 MDa HA were tested, 5 mg/ml as a high concentration to model 'healthy' tissue and 0.5 mg/ml as a pathological or diseased environment[8]. Phosphate buffered saline (PBS) without HA served as a negative control. Results of lubrication testing with HA found a dose-dependent decrease in friction coefficient with increasing HA concentration (FIGS. 13A and B). High concentration (5 mg/ml) HA resulted in the lowest $\mu_{kinetic}$ of 0.04 and $\mu_{static}$ of 0.07-0.15. The observed $\mu_{kinetic}$ in high concentration HA was of much greater than the physiologically observed coefficients of friction in the knee, but roughly agreed with previously published in vitro magnitudes, and was significantly lower than negative controls tested in PBS. Cartilage explants bathed in low concentration (0.5 mg/ml) HA produced a higher $\mu_{kinetic}$ that reached 0.11 and a $\mu_{static}$ of 0.17-0.24. Finally, control samples of cartilage tested in PBS without any exogenous HA had an average $\mu_{kinetic}$ of 0.17 after 1200 seconds of pre-test relaxation, slightly increasing to 0.18 at 1.2 seconds of pre-test relaxation. Control samples had a $\mu_{static}$ of 0.32 after 1200 seconds of relaxation, decreasing to 0.26 at short relaxation times. The observed decrease in $\mu_{static}$ for shorter relaxation times was universal among tested samples, with $\mu_{static}$ approaching the values of $\mu_{kinetic}$. These results confirm that HA has a beneficial impact on lubrication properties of cartilage tissue explants.

Figure 13:
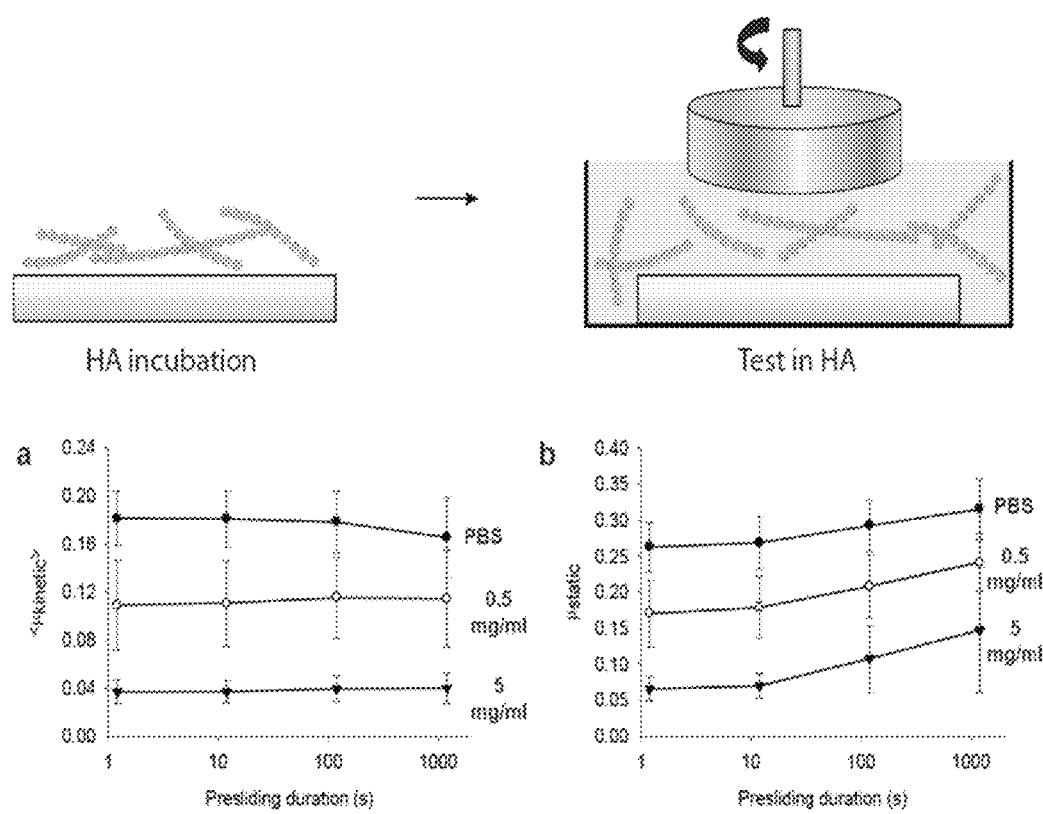
FIG. 13 shows cartilage surface-bound HA in the absence of an exogenous lubricant can recapitulate the friction coefficients of high concentration HA lubricants. 13a, Lubrication properties of native cartilage were tested in the presence of saline, low and high concentration HA after pre-test relaxation periods ranging from 1.2-1200 s. The kinetic friction $<\mu_{kinetic}>$ values decreased with increasing HA. 13b, The µstatic also exhibited an HA dose-dependent decrease across a range of pre-sliding durations, with values decreasing as pre-test relaxation time decreased. 13c, Cartilage explants were modified with the HA binding polymer system and exposed to HA solutions. After thorough washing, the lubrication properties were tested in PBS solution.

Since HA injected into a joint is quickly cleared and HA is in low concentration in a diseased environment, a key test of the polymer-modified hyaluronic acid-binding surface is the ability to retain the benefit of increased lubrication after HA is no longer present in the environment. HA-binding coatings without exogenous lubricant were able to replicate the low friction characteristics of native cartilage tested with physiological levels of HA lubricant (FIGS. 13 C and D). Cartilage surfaces treated with the HA-binding polymer system were incubated with low and high concentration HA solutions. After incubation, the tissue samples were thoroughly washed to remove any unbound HA and lubrication was tested in PBS without any HA. Cartilage treated with HA-binding coatings and pre-incubated low or high concentrations of HA were able to significantly improve the boundary lubrication compared to native cartilage without treatment. Tissue samples cultured with a low concentration HA had a $\mu_{kinetic}$ Of just 0.09-0.10 and $\mu_{static}$ of 0.15-0.24. Samples exposed to a high concentration of HA exhibited a $\mu_{kinetic}$ of 0.056 and $\mu_{static}$ range of 0.12-0.24. The magnitudes of $\mu_{kinetic}$ for cartilage surfaces treated with HA binding polymers and tested in PBS were similar to native, untreated cartilage tested in the presence of HA lubricants. This pivotal result suggests that most of the boundary lubrication effects can be replicated by surface-bound HA alone, without the need for large concentrations of HA in the local environment. The practical implication is that even in a pathological environment where low HA concentrations are present, the HA binding polymer coating can concentrate the limited HA available at the tissue surface and improve boundary lubrication. As HA bound to the tissue surface coatings was thoroughly washed before testing, the improved lubrication implies that a stable surface coating of HA is generated on the tissue that will not be quickly flushed from the joint. Although the previously observed affinity of HABPep for HA was fairly modest ($K_d$=1.65 μM), it is likely that the relatively large size of each HA molecule compared to the peptide resulted in multiple peptide interactions with each HA molecule, increasing the overall avidity[12].

The observed improvement in boundary lubrication with HA binding coatings was confirmed to be due to specific peptide-HA interactions. To rule out the potential effects of nonspecific HA adsorption on boundary lubrication, an unmodified cartilage sample was incubated in high concentration HA, thoroughly washed, and tested in PBS. The resultant surface had a $\mu_{kinetic}$ of 0.15-0.16 and a $\mu_{static}$ of 0.23-0.25, which was not significantly different from native control cartilage, indicating that nonspecific adhesion of HA to cartilage had minimal impact on tissue lubrication (data not shown). Additionally, to confirm that the PEG layer did not enhance the boundary lubrication of articular cartilage, a PEGylated cartilage sample was tested in the absence of HA. The resulting lubrication had a $\mu_{kinetic}$ of 0.16-0.17 and a $\mu_{static}$ of 0.25-0.29, again not significantly different from native unmodified controls (data not shown). Thus, neither non-specific HA binding nor PEGylation significantly changed the boundary lubrication of articular cartilage, implying that HA concentrated on the surface of cartilage through specific, noncovalent interactions with the HA binding polymers was responsible for improving boundary lubrication.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A hydrogel composition comprising:
   (a) a biomaterial comprising at least one biologically compatible polymer having one or more hyaluronic acid (HA) binding peptides selected from the group consisting of: GAHWQFNALTVR (SEQ ID NO: 1), CRRDDGAHWQFNALTVR (SEQ ID NO: 2) or a conservative amino acid substitution thereof at a residue position other than 4, 5, 6, 9, 10 or 11, GAAWQFNALTVR (SEQ ID NO: 3) or a conservative amino acid substitution thereof at a residue position other than 4, 5, 6, 9, 10 or 11, GAHWQFAALTVR (SEQ ID NO: 4) or a conservative amino acid substitution thereof at a residue position other than 4, 5, 6, 9, 10 or 11, and iv) GAHWQFNALTVA (SEQ ID NO: 5) or a conservative amino acid substitution thereof at a residue position other than 4, 5, 6, 9, 10 or 11,
   wherein said one or more HA binding peptides are covalently linked to the biologically compatible polymer, and
   (b) at least one other component, wherein the at least one other component is one or more second biocompatible polymers;
   wherein the first or second biocompatible polymer is selected from the group consisting of: poly(ethylene glycol), poly(propylene glycol), poly(methyl vinyl ether), oligoethylene, poly(isobutylene), poly(tetrahydrofuran), poly(oxytrimethylene), poly(dimethylsiloxane), poly(dimethylsilane), nylon 6, nylon 11, poly (acrylonitrile), squalane, poly(1,3-dioxolane), poly (iminooligomethylene), poly(L-lysine), polyethyleneimine, poly(adipate), poly(L-caprolactone), poly(L-lactic acid), and derivatives thereof; and wherein the biocompatible polymers are cross linked together to form a hydrogel.

2. The hydrogel composition of claim 1, wherein the biocompatible polymers are cross linked using a photoinitiator.

3. The hydrogel composition of claim 2, wherein the one or more first or second biocompatible polymers are mono- or disubstituted with an acrylate group.

4. The hydrogel composition of claim 1, wherein the hydrogel further comprises one or more isolated stem cells.

5. The hydrogel composition of claim 4, wherein said one or more isolated stem cells are selected from the group consisting of a mesenchymal stem cell, a cardiac stem cell, a liver stem cell, a retinal stem cell, a chondrocyte, an adipose tissue derived stem cell, and an epidermal stem cell.

6. A method of filling a tissue void on or in a subject in need thereof, said method comprising contacting said void with a therapeutically effective amount of the hydrogel composition of claim 4.

7. The method of claim 6, wherein the one or more isolated stem cells are autologous to the subject.

8. The method of claim 6, wherein the one or more isolated stem cells are allogeneic to the subject.

9. A therapeutic method for the treatment of eye diseases by means of an eye surgery treatment, comprising applying to the eye of a subject in need of such treatment a therapeutically effective amount of the hydrogel composition of claim 1.

10. The therapeutic method of claim 9, wherein the surgery treatment is selected from the group consisting of corneal transplantation, cataract surgery, glaucoma surgery, and surgery to repair retinal detachment.

11. A therapeutic method for the treatment of dry eye in a subject, comprising applying to the eye of a subject in need of such treatment a therapeutically effective amount of the hydrogel composition of claim 1.

12. A method of treating a cartilage defect in a tissue of a subject comprising administering to the tissue of the subject in need of treatment, a therapeutically effective amount of the hydrogel composition of claim 1.

13. The method of claim 12, wherein the defect is in cartilage in a joint or ligament of the subject.

14. A coating for a tissue surface comprising the hydrogel composition of claim 1.

15. The coating of claim 14, wherein the HA binding peptide (HABPep) is a peptide comprising the following amino acid sequence: GAHWQFNALTVR (SEQ ID NO: 1).

* * * * *